US008586757B2

(12) United States Patent
Mauduit et al.

(10) Patent No.: US 8,586,757 B2
(45) Date of Patent: *Nov. 19, 2013

(54) RUTHENIUM-BASED CATALYTIC COMPLEXES AND THE USE OF SUCH COMPLEXES FOR OLEFIN METATHESIS

(71) Applicant: Umicore AG & Co. KG, Hanau (DE)

(72) Inventors: Marc Mauduit, Vitre (FR); Isabelle Laurent, Rennes (FR); Hervé Clavier, Vannes (FR)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/736,236

(22) Filed: Feb. 13, 2013

(65) Prior Publication Data
US 2013/0144060 A1    Jun. 6, 2013

Related U.S. Application Data

(63) Continuation of application No. 12/517,322, filed as application No. PCT/EP2007/063062 on Nov. 30, 2007, now Pat. No. 8,394,965.

(30) Foreign Application Priority Data

Nov. 30, 2006  (FR) .................................. 06 10478
Jan. 30, 2007  (FR) .................................. 07 00634

(51) Int. Cl.
 *C07F 15/00*     (2006.01)
(52) U.S. Cl.
 USPC .................................. 548/103; 546/4; 556/22
(58) Field of Classification Search
 USPC .................................. 548/103; 546/4; 556/22
 See application file for complete search history.

(56) References Cited

U.S. PATENT DOCUMENTS 4,287,201 A    9/1981   Olson et al.

FOREIGN PATENT DOCUMENTS

| DE | 103 35 417 A1 | 2/2005 |
|---|---|---|
| WO | 94/05649 A | 3/1994 |
| WO | WO 02/14376 A2 | 2/2002 |
| WO | 03/044060 A | 5/2003 |
| WO | 2004/035596 A | 4/2004 |
| WO | WO 2004/035596 A1 | 4/2004 |

OTHER PUBLICATIONS

Michrowska, A. et al. (2004) "Nitro-Substituted Hoveyda-Grubss Ruthenium Carbenes: Enhancement of Catalyst Activity through Electronic Activation" J. Am. Chem. Soc. 126: 9318-9325.

Sashuk, V. et al. (2006) "Synthetic and Mechanistic Studies on Enyne Metathesis: A Catalyst Influence" J. of Molecular Catalysis A: Chemical. 257:59-66.

Mauduit, M. et al. (2010) Comparative Results of Catalyst 1 vs. Nitro-Catalyst 4 ("Grela-catalyst") Sciences Chimiques de Rennes, provided in corresponding EP 2007847578.

Mauduit, M. et al. (2010) Comparative Results of Catalyst 1b vs. Nitro-Catalyst 2 ("Grela-catalyst") Sciences Chimiques de Rennes, provided in corresponding EP 2007847578.

Mauduit, M. et al. (2010) Comparative Results of Catalyst M71-PCy3 (1) vs. Nitro-Catalyst 2 ("Grela-catalyst first generation") Sciences Chimiques de Rennes, provided in corresponding EP 2007847578.

International Preliminary Report on Patentability received in PCT/EP2007/063062, mailed Mar. 4, 2009. English translation provided.

Borre, E. et al. (2008) "Recent Advances for Controlling the Activity and the Recoverability of Hoveyda-Grubbs Type Olefin Metathesis Catalysts" Chemistry Today 26(5):89-92 (publication date after file date of U.S. Appl. No. 12/517,322, and as such are not prior art).

Borre, E. et al. (2011) "Terpenic Compounds as Renewable Sources of Raw Material for Cross-Metathesis" Synthesis 13:2125-2130 (publication date after file date of U.S. Appl. No. 12/517,322, and as such are not prior art).

Mohapatra, D. et al. (2010) "Catalytic Activity of Aminocarbonyl Group Containing Hoveyda-Grubbs-Type Complexes for the Syntheses of Hernarumin I and Stagonolide A" Synlett 8:1223-1226 (publication date after file date of U.S. Appl. No. 12/517,322, and as such are not prior art).

Budesinsky, Z. et al. (1954) "Tuberculostatics. IX. Allyl and Propenyl Derivatives of m-aminophenol" Collection of Czechoslovak Chemical Communications, Institute of Organic Chemistry & Biochemistry, 19:966-975. English abstract provided.

D. Rix, et al., "Activated pyridinium-tagged ruthenium complexes as efficient catalysts for ring-closing metathesis", Journal of Organometallic Chemistry 691, 2006, p. 5397-5405.

E. Borre, et al., "Design of a library of Hoveyda-Grubbs type olefin metathesis catalysts", Chemistry Today, vol. 27, No. 5, Sep.-Oct. 2009, p. 74-78.

D. Rix, et al., "Aminocarbonyl Group Containing Hoveyda-Grubbs-Type Complexes: Synthesis and Activity in Olefin Metathesis Transformations", Journal of Organometallic Chemistry, vol. 73, No. 11, 2008, p. 4225-4228.

H. Clavier, et al., "Towards Long-Living Metathesis Catalysts by Tuning the N-Heterocyclic Carbene (NHC) Ligand on Trifluoroacetamide-Activated Boomerang Ru Complexes", Eur. Journal of Organometallic Chemistry, 2009, p. 4254-4265.

International Search Report issued in corresponding International Application No. PCT/EP2007/063062 filed on Nov. 30, 2007.

*Primary Examiner* — Bernard Dentz
(74) *Attorney, Agent, or Firm* — Smith, Gambrell & Russell, LLP

(57) ABSTRACT

Disclosed herein are compounds of the formula (I) or (II) in which: L is a neutral ligand; X, X' are anionic ligands; $R^1$ and $R^2$ are, separately, a hydrogen, a $C_1$-$C_6$ alkyl, a $C_1$-$C_6$ perhalogenoalkyl, a aldehyde, a ketone, an ester, a nitrile, an aryl, a pyridinium alkyl, an optionally substituted $C_5$ or $C_6$ pyridinium alkyl, perhalogenoalkyl or cyclohexyl, a $C_nh2_NY$ radical 10 with n between 1 and 6 and y an iconic marker, or a radical having the formula: wherein $R^1$ can be a radical of formula (Ibis) when the compound has formula (I) or of formula (IIbis) when the compound has formula (II), $R^3$ is a $C_1$-$C_6$ alkyl, or a $C_5$ or $C_6$ cycloalkyl or a $C_5$ or $C_6$ aryl; $R^0$, $R^4$, $R^5$, $R^6$, $R^7$, $R^8$, $R^9$, $R^{10}$, $R^{11}$, are, separately, a hydrogen, $C_1$-$C_6$ alkyl, a $C_1$-$C_6$ perhalogenoalkyl, or a $C_5$ or $C_6$ aryl; wherein $R^9$, $R^{10}$, $R^{11}$ can be a heterocycle; $X^1$ is anion. $R^1$ and $R^2$ can form, with the N and the C to which they are attached, a heterocycle.

23 Claims, 11 Drawing Sheets

RUTHENIUM-BASED CATALYTIC COMPLEXES AND THE USE OF SUCH COMPLEXES FOR OLEFIN METATHESIS

INTRODUCTION AND BACKGROUND

This invention relates to new activated and recyclable ruthenium-based catalytic complexes as well as a method for synthesis of same.

The invention also relates to the use of such catalytic complexes for olefin metathesis.

The development of recyclable or activated ruthenium-based catalytic complexes is based on the work of R. Grubbs of the University of California (USA) relating to the ruthenium complex 2a (precatalyst 2b) called the Grubbs II catalyst.

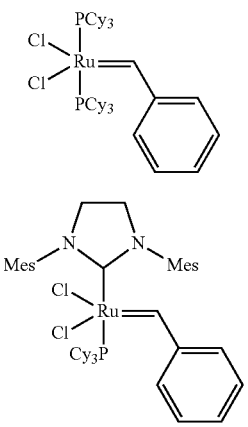

Thus, the first recyclable complex 3a (precatalyst 3b) with a styrenyl ether ligand (called a "boomerang" ligand) was described by Hoveyda of the University of Boston (USA).

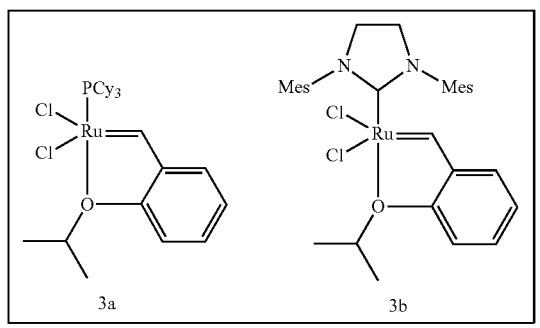

WO0214376

This compound is described in particular in the international patent application WO 0214376.

A first advantage of this complex is that it enables recycling of the precatalyst, which is recovered at the end of the reaction and can be reused.

However, this catalyst has the disadvantage of leading to significant losses, in an amount of 10% per cycle.

A second advantage of this complex is that it minimizes the presence of toxic metal residue (ruthenium) in the reaction products.

However, this complex is less active than the Grubbs 2b complex described above.

The first activated complex 4 was described in 2002, based on the electronic effect produced by the presence of a nitro group ($NO_2$) on the Hoveyda styrenyl ether ligand described above.

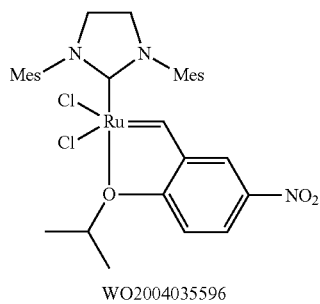

WO2004035596

This activated complex is described in the international patent application WO 2004 035596.

The activation of this precatalyst is based on the significantly accelerated detachment of the styrenyl ether ligand, which causes a rapid initiation of the catalytic cycle and therefore a significant increase in the reaction kinetics. The reactions can then take place under gentler conditions, in practice at room temperature, and with lower catalytic loads.

However, this complex is not easily recycled, and thus leads to significant toxic metal residue (ruthenium) contamination in the reaction products. Such a disadvantage is particularly detrimental to the synthesis of certain high added value products such as pharmaceutical molecules.

According to the prior art, it therefore appears that reactivity and recycling of such ruthenium complexes are two antinomic properties since, in practice, the increase in the activity is achieved at the expense of the recycling, and, conversely, the increase in recycling is achieved at the expense of the reactivity of the catalytic species.

SUMMARY OF THE INVENTION

The objective of this invention is to describe activated and recyclable ruthenium complexes in which the compromise between these antinomic properties can be optimized, i.e. complexes capable of having an excellent activity while preserving good recycling.

An objective of this invention is therefore to propose such complexes which use can enable a decrease in the catalytic load. Such an objective is important in consideration of the high cost of these catalysts.

An objective of this invention is therefore to propose such complexes which degree of recyclability leads to a significant reduction in the toxic metal waste in the end products.

In the best of cases, the catalysts according to this invention will enable products to be obtained with a very low ruthenium content, in practice below 10 to 20 ppm.

These objectives are achieved by the invention, which relates to any compound of formula (I) or (II):

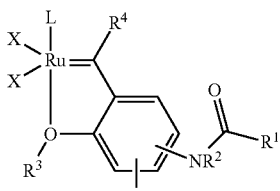
(I)

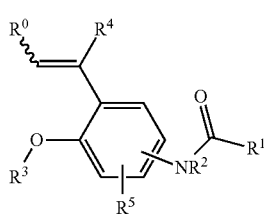
(II)

in which:
L is a neutral ligand;
X, X' are anionic ligands;
$R^1$ and $R^2$ are, independently, an hydrogen, a $C_1$ to $C_6$ alkyl, a $C_1$ to $C_6$ perhalogenoalkyl, an aldehyde, a ketone, an ester, an amide, a nitrile, an optionally substituted aryl, a pyridinium alkyl, a pyridinium perhalogenoalkyl or an optionally substituted $C_5$ or $C_6$ cyclohexyl, a $C_nH_{2n}Y$ or $C_nF_{2n}Y$ radical with n being between 1 and 6 and Y being an ion marker, or a radical of formula:

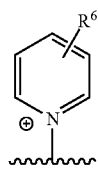 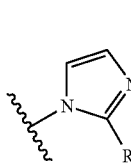 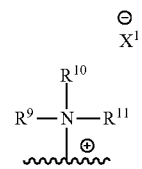

$R^1$ can be a radical of formula (Ibis) when the compound is of formula I:

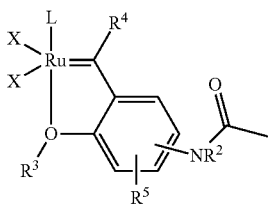
(Ibis)

or of formula (II bis) when the compound is of formula (II):

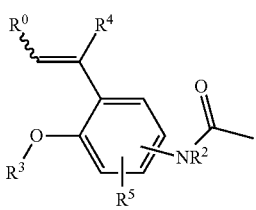
(IIbis)

$R^3$ is a $C_1$ to $C_6$ alkyl or a $C_5$ or $C_6$ cycloloalkyl or a $C_5$ or $C_6$ aryl;

$R^0$, $R^4$, $R^5$, $R^6$, $R^7$, $R^8$, $R^9$, $R^{10}$, $R^{11}$ are, independently, an hydrogen, a $C_1$ to $C_6$ alkyl, a $C_1$ to $C_6$ perhalogenoalkyl, or a $C_5$ or $C_6$ aryl; $R^9$, $R^{10}$, $R^{11}$ can form a heterocycle;

$X^1$ is an anion: halogen, tetrafluoroborate ($[BF_4]^-$), [tetrakis-(3,5-bis-(trifluoromethyl)-phenyl)borate] ($[BARF]^-$), hexafluorophosphate ($[PF_6]^-$), hexafluoroantimoine ($[SbF_6]^-$), hexafluoroarsenate ($[AsF_6]^-$), trifluoromethylsulfonate ($[(CF_3)_2N]^-$);

$R^1$ and $R^2$ can form with the N and the C to which they are attached a heterocycle of formula:

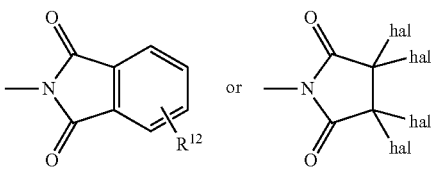

wherein hal is an halogen and $R^{12}$ is an hydrogen, a $C_1$ to $C_6$ alkyl, or a $C_5$ or $C_6$ cycloalkyl or a $C_5$ or $C_6$ aryl.

Preferably, L is $P(R^{13})_3$, with $R^{13}$ being a $C_1$ to $C_6$ alkyl or an aryl or a $C_5$ or $C_6$ cycloalkyl.

Also preferably, L is a ligand of formula 7a, 7b, 7c, 7d or 7e:

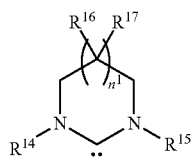
7a

7b

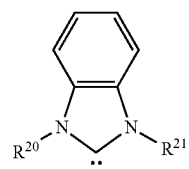
7c

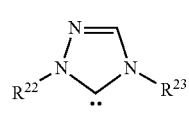
7d

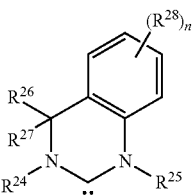
7e in which: $n^1$=0, 1, 2, 3;
$R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ are independently a $C_1$ to $C_6$ alkyl, a $C_3$ to $C_{20}$ cycloalkyl, a $C_2$ to $C_{20}$ alkenyl, a naphthyl, an anthracene or a phenyl, wherein said phenyl can be substituted by up to 5 groups chosen from the $C_1$ to $C_6$ alkyls, the $C_1$ to $C_6$ alkoxys and the halogens; $R^{16}$ and $R^{17}$, and $R^{26}$ and $R^{27}$ can form a cycle with 3, 4, 5, 6, or 7 links; $R^{26}$ can independently form an aromatic cycle with 6 conjoined links.

Advantageously, L is $PCy_3$, with Cy being cyclohexyl, or L is a ligand of formula 7a or 7b. X is a chlorine, and X' is a chlorine.

The ion marker Y is preferably chosen from the group consisting of:

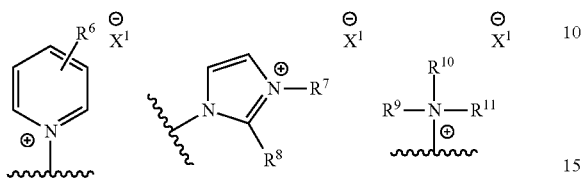

According to an alternative, the compound according to the invention satisfies formula (I) in which $R^1$ is chosen from the group consisting of $CH_3$, $CF_3$, $C_6F_5$, $pNO_3C_6H_4$.

According to an alternative, the compound satisfies formula 1a:

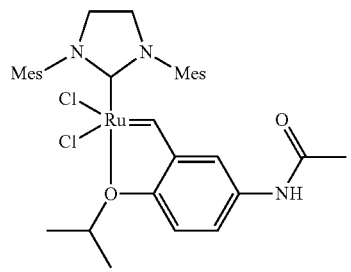

According to another alternative, the compound satisfies formula 1b:

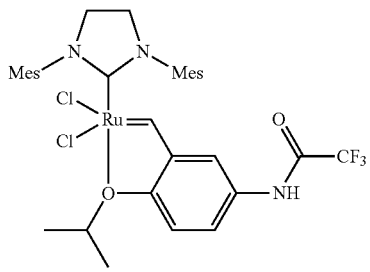

According to another alternative, the compound satisfies formula 1c:

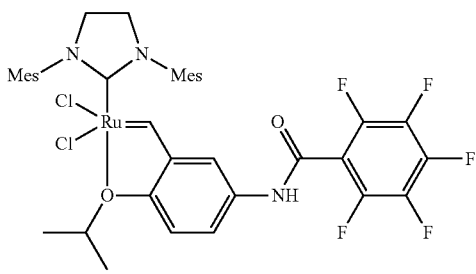

According to another alternative, the compound satisfies formula 1d:

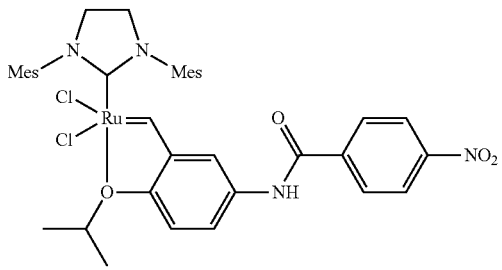

According to another alternative, the compound satisfies formula 1e:

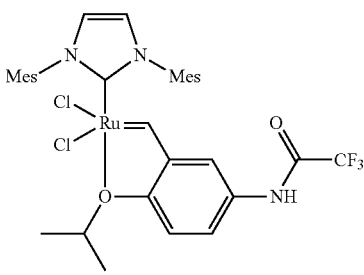

According to another alternative, the compound satisfies formula 1f:

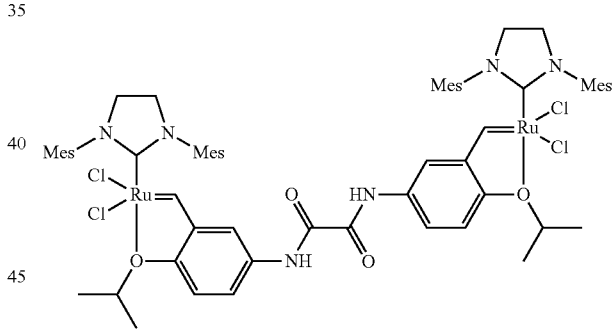

According to another alternative, the compound satisfies formula 1g:

1g

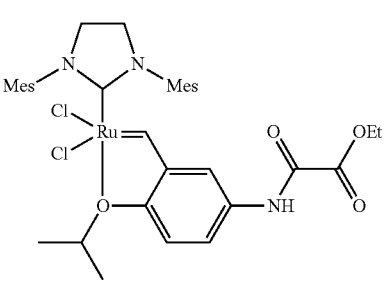

According to another alternative, the compound satisfies formula 1h:

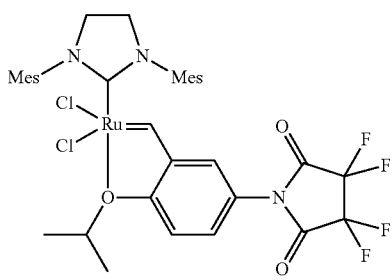

1h

According to another alternative, the compound satisfies formula 1i:

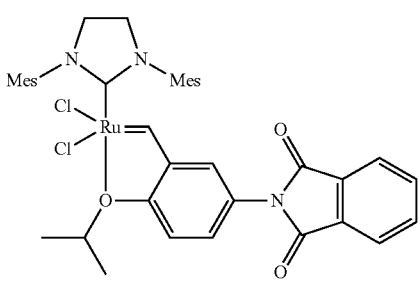

1i

According to another alternative, the compound satisfies formula 1j:

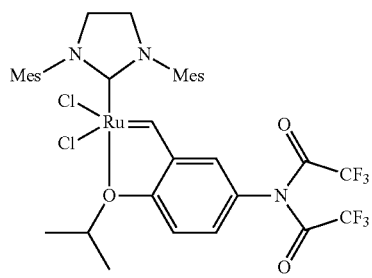

1j

According to another alternative, the compound satisfies formula 1k:

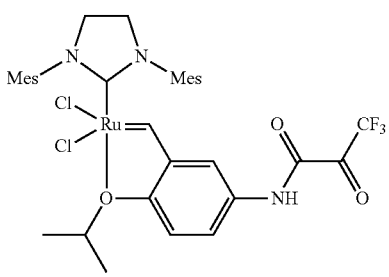

1k

According to another alternative, the compound satisfies formula 11:

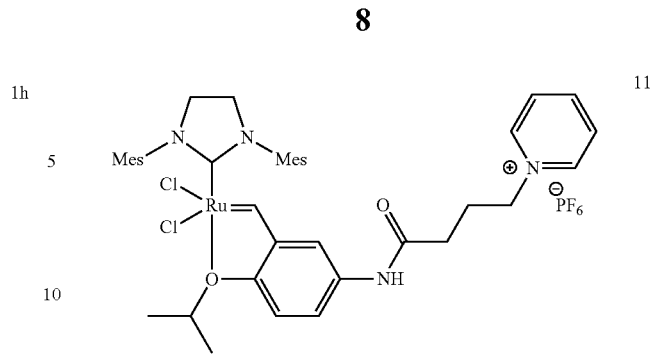

11

According to another alternative, the compound satisfies formula 12:

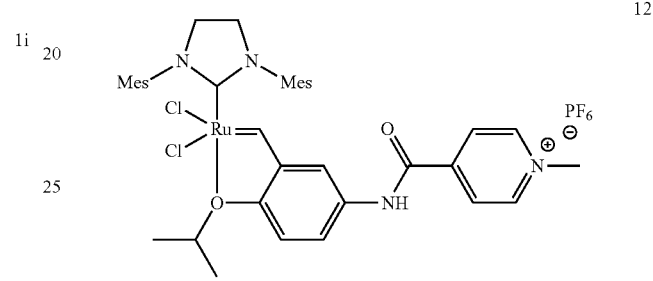

12

According to another alternative, the compound satisfies formula 13:

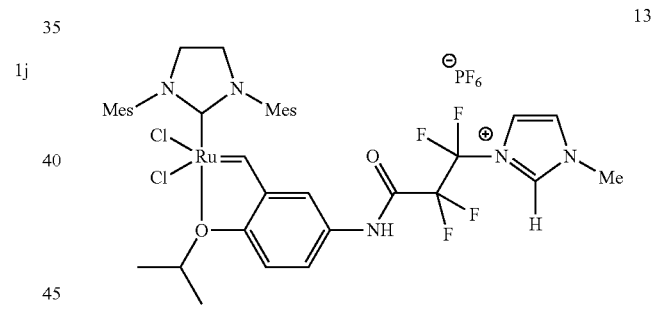

13

According to another alternative, the compound satisfies formula 14:

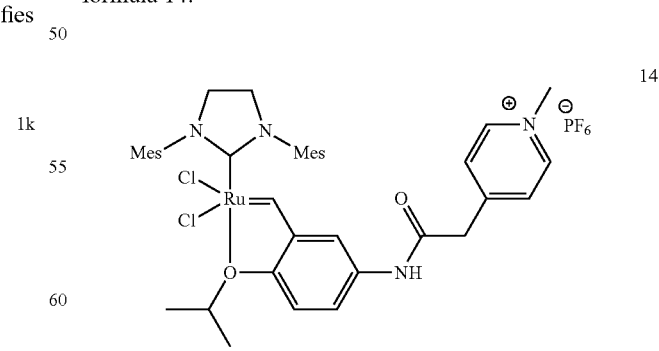

14

The invention also relates to any method for the synthesis of a compound of formula (I) characterized in that it includes a first step consisting of reacting 4-isopropoxy-3-vinylaniline with a compound having an acyl function so as to obtain an amide ligand and a second step consisting of reacting said amide ligand with a compound of formula (III):

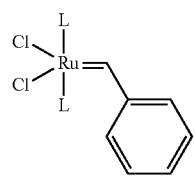

Preferably, said compound of formula (III) is the Grubbs precatalyst (2b) or the Nolan precatalyst (2c).

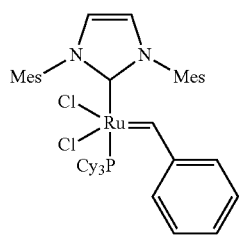

The introduction, according to the invention, of an amide function on the styrenyl ether ligand has the specially promotes the activation of the catalyst.

In particular, when the amide function has a perfluorinated methyl (trifluoromethyl), a significant activation of the catalyst is observed and is characterized by relatively high conversions in very short amounts of time. Under these conditions, an economic impact can be envisaged by significantly reducing the catalytic load in the metathesis reactions without affecting the yield.

In addition, this amide function can act as a spacer for the introduction of an ion marker ("tag") for immobilization in the aqueous and/or ion phase as well as on a solid support.

Such an ion marking enables better recycling of the catalytic complexes to be performed in aqueous/ion solvents or on a solid support (continuous flow reaction) and enables a clear reduction in the cost of the reaction while avoiding contamination of high added value products, in particular in the context of a pharmaceutical molecule synthesis process.

The invention, as well as the various advantages thereof, will be easier to understand in view of the following description of various examples of embodiments thereof provided in reference to the figures.

LEGEND

FIGS. 1 through 5

Figure 1:
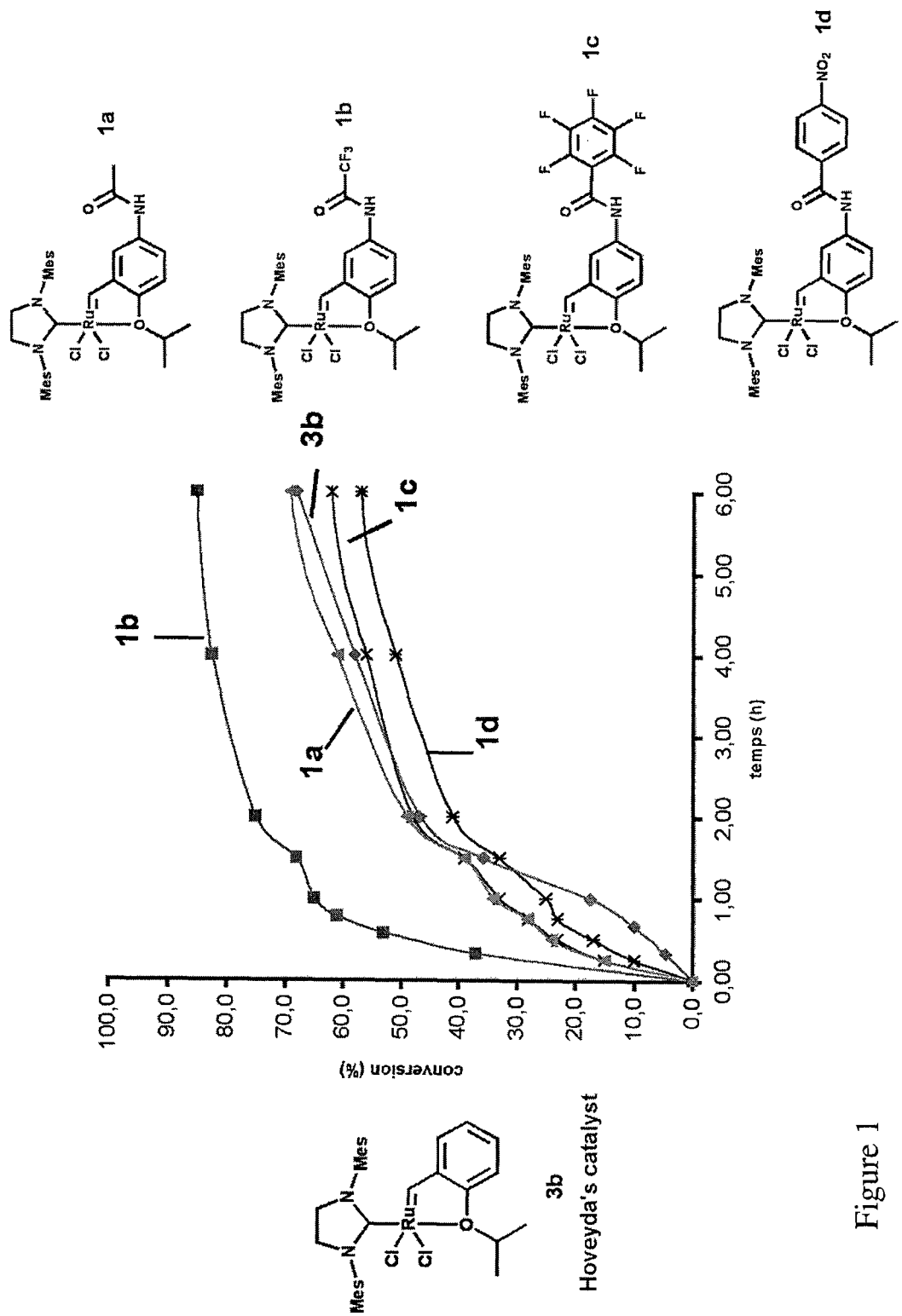
FIG. 1 is a graph showing the conversion rate over time of a metallyl-allyl diethyl malonate compound in the context of a metathesis cyclization reaction at room temperature, in the presence of 1 mol % of the Hoveyda complex 3b on one hand and in the presence of 1 mol % of catalytic complexes according to the invention 1a, 1b, 1c and 1d on the other hand.

| conversion temps | conversion time |
|---|---|

DETAILED DESCRIPTION OF INVENTION

First, the synthesis of the various examples of complexes according to the invention will be described below.

The complexes 1a, 1b, 1c, 1d, 1e and 1f according to the invention are obtained in two steps from the functionalized aniline 5.

The 4-step method of synthesis of this functionalized aniline 5 from para-nitro-phenol is described in the article "Activated pyridinium-tagged ruthenium complex as efficient catalyst for Ring-Closing Metathesis." D. Rix, H. Clavier, Y. Coutard, L. Gulajski, K. Grêla*, M. Mauduit*, J. Organomet. Chem., 2006, 691, 5397-5405.

The following diagram summarizes this synthesis in two steps:

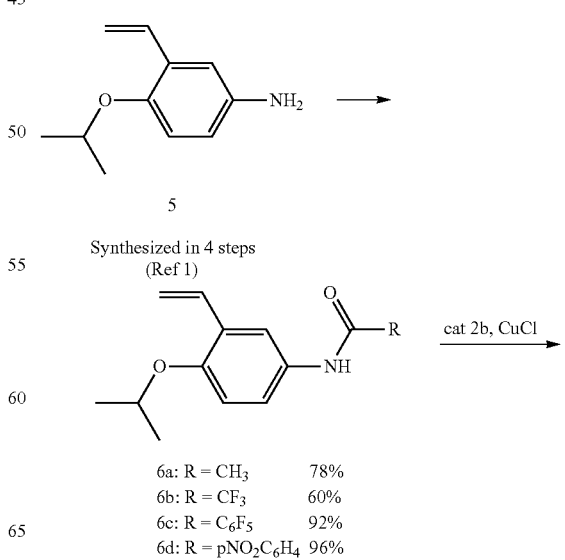

-continued

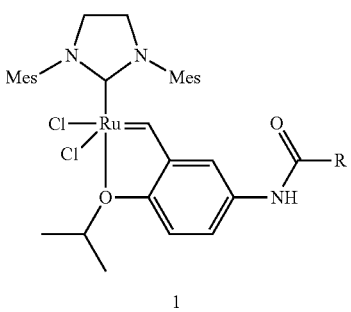

1

| 1a: R = CH₃ | 98% |
| 1b: R = CF₃ | 91% |
| 1c: R = C₆F₅ | 50% |
| 1d: R = pNO₂C₆H₄ | 95% |

$1^{st}$ step: synthesis of amides 6a, 6b, 6c, 6d, 6f, 9a, 9b, 10a and 10b from 4-isopropoxy-3-vinylaniline 5

According to a general procedure, 4-isopropoxy-3-vinylaniline 5 (1 eq.; around 0.2 mmol) is introduced into a round-bottom flask, placed under nitrogen, and solubilized in anhydrous dichloromethane (2-3 mL). Pyridine (1.5 eq.) is added to the solution, which is then cooled to 0° C. Acyl chloride or anhydride (1.2 eq) is then slowly added, then the reaction medium is agitated at room temperature under nitrogen for 2 hours.

The raw material is then diluted with dichloromethane (10 mL), washed with an aqueous hydrochloric acid solution 1N (2 mL), then with a saturated sodium hydrogen carbonate solution (2×2 mL) and finally with a saturated sodium chloride solution (3×2 mL). The organic phases are collected, dried on magnesium sulfate and concentrated under vacuum.

The residue is purified by chromatography on silica gel.

Synthesis of the
N-(4-isopropoxy-3-vinylphenyl)acetamide
compound 6a

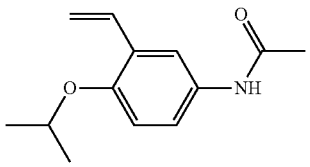 [SMILES: C=Cc1cc(NC(C)=O)ccc1OC(C)C]

Using the general procedure for obtaining amides from 4-isopropoxy-3-vinylaniline 5 (50 mg; 0.3 mmol) and with acetyl chloride (15 μL), acetamide is obtained after chromatography on silica gel (eluent: CH₂Cl₂/AcOEt (4:1)) in the form of a pink solid (49 mg, 78%).

Rf (CH₂Cl₂/AcOEt (4:1))=0.48

NMR $^1$H (400 MHz, CDCl₃) δ (ppm): 7.54 (s, 1H, NH); 7.51 (d, 1H, $^4J$=2.7 Hz, H₇); 7.38 (dd, 1H, $^3J$=8.8 Hz, $^4J$=2.7 Hz, H₅); 6.99 (dd, 1H, $^3J_{cis}$=11.2 Hz, $^3J_{trans}$=17.8 Hz, H₉); 6.81 (d, 1H, $^3J$=8.8 Hz, H₄); 5.68 (dd, 1H, $^2J_{gem}$=1.4 Hz, $^3J_{trans}$=17.8 Hz, H₁₀ₐ); 5.22 (dd, 1H, $^2J_{gem}$=1.4 Hz, $^3J_{cis}$=11.2 Hz, H₁₀ᵦ); 4.45 (sept., 1H, $^3J$=6.1 Hz, H₂); 2.14 (s, 3H, H₁₁); 1.31 (d, 6H, $^3J$=6.1 Hz, H₁)

NMR $^{13}$C (100 MHz, CDCl₃) δ (ppm): 168.4 (C=O); 152.0 (C3); 131.4 (C9); 131.1 (C8); 128.3 (C6); 121.2 (C7); 118.6 (C5); 115.1 (C4); 114.5 (C10); 71.4 (C2); 24.3 (C11); 22.1 (C1).

Synthesis of the
N-(4-isopropoxy-3-vinylphenyl)trifluoroacetamide
compound 6b

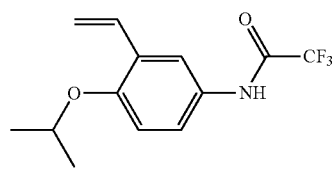 [SMILES: C=Cc1cc(NC(=O)C(F)(F)F)ccc1OC(C)C]

Using the general procedure for obtaining amides from 4-isopropoxy-3-vinylaniline 5 (26 mg; 0.14 mmol) and with trifluoroacetic anhydride (25 μL), trifluoroacetamide is obtained after chromatography on silica gel (eluent: CH₂Cl₂/EP (9:1)) in the form of a yellowish solid (23 mg, 59%).

Rf (CH₂Cl₂/EP (9:1))=0.65

NMR $^1$H (400 MHz, CDCl₃) δ (ppm): 7.93 (s, 1H, NH); 7.59 (d, 1H, $^4J$=2.7 Hz, H₇); 7.44 (dd, 1H, $^3J$=8.9 Hz, $^4J$=2.7 Hz, H₅); 7.01 (dd, 1H, $^3J_{cis}$=11.2 Hz, $^3J_{trans}$=17.8 Hz, H₉); 6.88 (d, 1H, $^3J$=8.9 Hz, H₄); 5.74 (dd, 1H, $^2J_{gem}$=1.3 Hz, $^3J_{trans}$=17.9 Hz, H₁₀ₐ); 5.28 (dd, 1H, $^2J_{gem}$=1.3 Hz, $^3J_{cis}$=11.2 Hz, H₁₀ᵦ); 4.53 (sept., 1H, $^3J$=6.1 Hz, H₂); 1.35 (d, 6H, $^3J$=6.1 Hz, H₁)

NMR $^{19}$F (376.5 MHz, CDCl₃) δ (ppm): −76.1 (s, 3F, F₁₄)

NMR $^{13}$C (100 MHz, CDCl₃) δ (ppm): 155.7 (quad., $^2J_{C-F}$=37 Hz, C=O); 153.3 (C3); 131.0 (C9); 128.7 (C8); 127.9 (C6); 121.2 (C7); 119.0 (C5); 115.8 (quad., $^1J_{C-F}$=288 Hz, C11); 115.3 (C4); 114.7 (C10); 71.3 (C2); 22.1 (C1)

Synthesis of the
N-(4-isopropoxy-3-vinylphenyl)pentafluorobenzamide
compound 6c

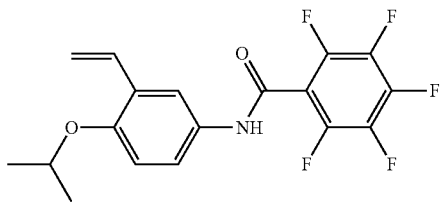 [SMILES: C=Cc1cc(NC(=O)c2c(F)c(F)c(F)c(F)c2F)ccc1OC(C)C]

Using the general procedure for obtaining amides from 4-isopropoxy-3-vinylaniline 5 (39 mg; 0.22 mmol) and with pentafluorobenzoyl chloride (38 μL), pentafluorobenzamide is obtained after chromatography on silica gel (eluent: CH₂Cl₂/EP (9:1)) in the form of a pink solid (75 mg, 92%).

Rf (CH₂Cl₂/EP (9:1))=0.71

NMR $^1$H (400 MHz, CDCl₃) δ (ppm): 7.70 (5, 1H, NH); 7.59 (d, 1H, $^4J$=2.7 Hz, H₇); 7.46 (dd, 1H, $^3J$=8.9 Hz, $^4J$=2.7 Hz, H₅); 7.02 (dd, 1H, $^3J_{cis}$=11.2 Hz, $^3J_{trans}$=17.8 Hz, H₉); 6.87 (d, 1H, $^3J$=8.9 Hz, H₄); 5.73 (dd, 1H, $^2J_{gem}$=1.3 Hz, $^3J_{trans}$=17.9 Hz, H₁₀ₐ); 5.27 (dd, 1H, $^2J_{gem}$=1.3 Hz, $^3J_{cis}$=11.2 Hz, H₁₀ᵦ); 4.52 (sept., 1H, $^3J$=6.1 Hz, H₂); 1.35 (d, 6H, $^3J$=6.1 Hz, H₁)

NMR $^{19}$F (376.5 MHz, CDCl$_3$) δ(ppm): −140.5 (d, 2F, $^3J_{F\text{-}F}$=16 Hz, F$_{72}$); −150.5 (t, 1F, $^3J_{F\text{-}F}$=20 Hz, F$_{14}$); −160.1 (dt, 2F, $^3J_{F\text{-}F}$=20 Hz, $^3J_{F\text{-}F}$=15 Hz, F$_{13}$)

NMR $^{13}$C (100 MHz, CDCl$_3$) δ (ppm): 155.2 (C=O); 152.9 (C3); 145.5-142.9-138.9-136.4 (C12, C13, C14); 131.1 (C9); 129.6 (C8); 128.6 (C6); 121.2 (C7); 119.0 (C5); 115.1 (C4); 114.8 (C10); 111.6 (C11); 71.4 (C2); 22.1 (C1)

Synthesis of the N-(4-isopropoxy-3-vinylphenyl/)paranitrobenzamide compound 6d

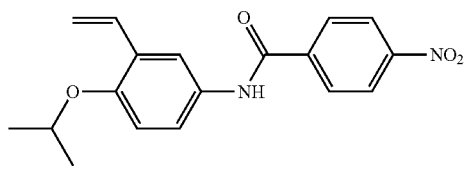

Using the general procedure for obtaining amides from 4-isopropoxy-3-vinylaniline 5 (38 mg; 0.22 mmol) and with paranitrobenzoyl chloride (48 mg), paranitrobenzamide is obtained after chromatography on silica gel (eluent: CH$_2$Cl$_2$) in the form of a yellow oil (67 mg, 96%).

Rf (CH$_2$Cl$_2$)=0.43

NMR $^1$H (400 MHz, CDCl$_3$) δ (ppm): 8.44 (s, 1H, NH); 8.17 (d, 2H, $^3$J=8.8 Hz, H$_{12}$); 7.96 (d, 2H, $^3$J=8.8 Hz, H$_{13}$); 7.61 (d, 1H, $^4$J=2.5 Hz, H$_7$); 7.45 (dd, 1H, $^3$J=8.8 Hz, $^4$J=2.5 Hz, H$_5$); 6.97 (dd, 1H, $^3J_{cis}$=11.2 Hz, $^3J_{trans}$=17.8 Hz, H$_9$); 6.80 (d, 1H, $^3$J=8.8 Hz, H$_4$); 5.63 (dd, 1H, $^2J_{gem}$=1.3 Hz, 3J$_{trans}$=17.7 Hz, H$_{10a}$); 5.20 (dd, 1H, $^2J_{gem}$=1.3 Hz, $^3J_{cis}$=11.1 Hz, H$_{10b}$); 4.48 (sept., 1H, $^3$J=6.1 Hz, H$_2$); 1.33 (d, 6H, $^3$J=6.1 Hz, H$_1$)

NMR $^{13}$C (100 MHz, CDCl$_3$) δ (ppm): 164.0 (C=O); 152.7 (C3); 149.4 (C14); 140.3 (C11); 131.2 (C9); 130.1 (C8); 128.3 (C6); 128.2 (C12); 123.7 (C13); 121.8 (C7); 119.4 (C5); 114.7 (C4); 114.6 (C10); 71.2 (C2); 22.0 (C1)

Synthesis of the N,N'-bis(4-isopropoxy-3-vinylphenyl)oxamide compound 6f

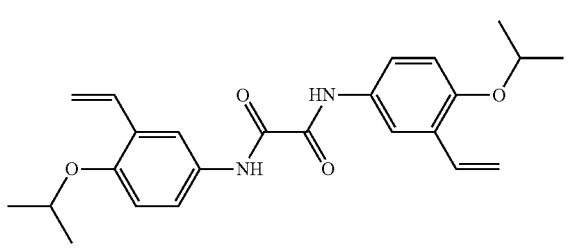 [SMILES: C=Cc1cc(NC(=O)C(=O)Nc2ccc(OC(C)C)c(C=C)c2)ccc1OC(C)C]

4-isopropoxy-3-vinylaniline 5 (30m; 1 eq.; 0.2 mmol) is introduced into a round-bottom flask, placed under nitrogen, and solubilized in anhydrous dichloromethane (3 mL). Pyridine (21 μL, 1.5 eq.) is added to the solution, which is then cooled to 0° C. Oxalyl chloride (8.8 μL; 1.2 eq.) is then slowly added, then the reaction medium is agitated at room temperature under nitrogen for 2 hours.

The raw material is diluted with dichloromethane (10 mL), washed with an aqueous solution of hydrochloric acid 1N (2 mL) then with a saturated sodium hydrogen carbonate solution (2×2 mL) and finally with a saturated sodium chloride solution (3×2 mL). The organic phases are collected, dried on magnesium sulfate and concentrated under vacuum.

The residue is purified by chromatography on silica gel (eluent: CH$_2$Cl$_2$/EP (9:1)) to produce the desired compound 6f in the form of a white solid (14 mg, 20%).

Rf (CH$_2$Cl$_2$/EP (9:1))=0.66

NMR $^1$H (400 MHz, CDCl$_3$) δ (ppm): 9.30 (s, 2H, NH); 7.75 (d, 2H, $^4$J=2.7 Hz, H$_7$); 7.55 (dd, 2H, $^3$J=8.9 Hz, $^4$J=2.7 Hz, H$_5$); 7.04 (dd, 2H, $^3J_{cis}$=11.2 Hz, $^3J_{trans}$=17.8 Hz, H$_9$); 6.89 (d, 2H, $^3$J=8.9 Hz, H$_4$); 5.76 (dd, 2H, $^2J_{gem}$=1.3 Hz, $^3J_{trans}$=17.9 Hz, H$_{10a}$); 5.29 (dd, 2H, $^2J_{gem}$=1.3 Hz, $^3J_{cis}$=11.2 Hz, H$_{10b}$); 4.53 (sept., 2H, $^3$J=6.1 Hz, H$_2$); 1.35 (d, 12H, $^3$J=6.1 Hz, H$_1$)

NMR $^{13}$C (100 MHz, CDCl$_3$) δ (ppm): 157.3 (C=O); 152.8 (C3); 131.2 (C9); 129.4 (C8); 128.6 (C6); 120.4 (C7); 118.2 (C5); 115.1 (C4); 114.9 (C10); 71.3 (C2); 22.1 (C1)

Synthesis of the N-(4-isopropoxy-3-vinylphenyl) difluorochloroacetamide compound 9a

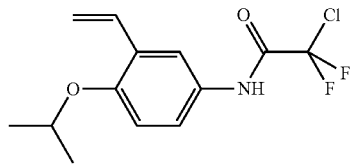 [SMILES: C=Cc1cc(NC(=O)C(F)(F)Cl)ccc1OC(C)C]

Using the general procedure for obtaining amides from 4-isopropoxy-3-vinylaniline 5 (50 mg; 0.3 mmol) and with 2-chloro-2.2-difluoroethanoic anhydride (63 μL), acetamide is obtained after chromatography on silica gel (eluent: CH$_2$Cl$_2$/AcOEt (4:1)) in the form of a pink solid (65 mg, 75%).

Rf (CH$_2$Cl$_2$/EP (4:1))=0.75

NMR $^1$H (400 MHz, CDCl$_3$) δ (ppm): 7.54 (s, 1H, NH); 7.59 (d, 1H, $^4$J=2.7 Hz, H$_7$); 7.43 (dd, 1H, $^3$J=8.8 Hz, $^4$J=2.7 Hz, H$_5$); 6.99 (dd, 1H, $^3J_{cis}$=11.2 Hz, $^3J_{trans}$=17.8 Hz, H$_9$); 6.86 (d, 1H, $^3$J=8.8 Hz, H$_4$); 5.70 (dd, 1H, $^2J_{gem}$=1.4 Hz, $^3J_{trans}$=17.8 Hz, H$_{10a}$); 5.27 (dd, 1H, $^2J_{gem}$=1.4 Hz, $^3J_{cis}$=11.2 Hz, H$_{10b}$); 4.50 (sept., 1H, $^3$J=6.1 Hz, H$_2$); 1.34 (d, 6H, $^3$J=6.1 Hz, H$_1$)

NMR $^{19}$F (376.5 MHz, CDCl$_3$) δ (ppm): −64.3 (s, 2F, CF$_2$)

NMR $^{13}$C (100 MHz, CDCl$_3$) δ (ppm): 158.8 (C=O); 153.2 (C3); 131.0 (C9); 128.6 (C8); 128.1 (C6); 122.2 (CF$_2$Cl); 121.2 (C5); 119.1 (C4); 116.2 (CF$_2$Cl); 114.7 (C10); 71.3 (C2); 22.0 (C1)

Synthesis of the 3-{1,1-difluoro-2-[4-isopropoxy-3-vinylphenylamino]-2-oxoethyl}-1-methyl-1H-imidazol-3-ium compound 9c

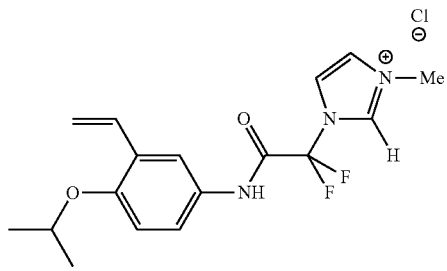 [SMILES: [Cl-] ; C=Cc1cc(NC(=O)C(F)(F)n2cc[n+](C)c2)ccc1OC(C)C]

Chlorinated amide 9a (20 mg; 0.07 mmol) is solubilized in anhydrous toluene (2.5 mL). N-methylimidazole (1 mL; 20 eq.) is added to the solution, which is then brought to reflux overnight. The volatile phases are then removed under reduced pressure and the tagged compound is recovered in the form of a dark orange oil.

NMR $^1$H (400 MHz, CDCl$_3$) δ (ppm): 9.49 (s, 1H, NH); 7.67 (d, 1H, $^4$J=2.7 Hz, H$_7$); 7.48 (dd, 1H, $^3$J=8.8 Hz, $^4$J=2.7 Hz, H$_5$); 7.43 (s, 1H, H$_{11}$); 7.04 (s, 1H, H$_{12}$); 7.00 (dd, 1H, $^3$J$_{cis}$=11.2 Hz, $^3$J$_{trans}$=17.8 Hz, H$_9$); 6.89 (s, 1H, H$_{13}$); 6.86 (d, 1H, $^3$J=8.8 Hz, H$_4$); 5.70 (dd, 1H, $^2$J$_{gem}$=1.4 Hz, $^3$J$_{trans}$=17.8 Hz, H$_{10a}$); 5.25 (dd, 1H, $^2$J$_{gem}$=1.4 Hz, $^3$J$_{cis}$=11.2 Hz, H$_{10b}$); 4.52 (sept., 1H, $^3$J=6.1 Hz, H$_2$); 3.68 (s, 3H, H$_{14}$); 1.33 (d, 6H, $^3$J=6.1 Hz, H$_1$)

NMR $^{19}$F (376.5 MHz, CDCl$_3$) δ (ppm): −64.0 (s, 2F, CF$_2$)

NMR $^{13}$C (100 MHz, CDCl$_3$) δ (ppm): 157.2 (C=O); 153.0 (C3); 131.1 (C9, C11); 128.8 (C8); 128.4 (C6); 121.5 (C5); 119.3 (C4); 119.1 (CF$_2$); 114.8 (C10); 114.6 (C7); 71.3 (C2); 33.3 (C14); 22.0 (C1)

Synthesis of the
3-chloro-2.2.3.3-tetrafluoro-7V-(4-isopropoxy-3
vinylphenyl)propanamide compound 9b Using the general procedure for obtaining amides from 4-isopropoxy-3-vinylaniline 5 (50 mg; 0.3 mmol) and with 3-chloro-2.2.3.3-tetrafluoropropanoyl chloride (81 mg), acetamide is obtained after chromatography on silica gel (eluent: CH$_2$Cl$_2$/AcOEt (4:1)) in the form of a white solid (65 mg, 57%).

Rf (CH$_2$Cl$_2$/AcOEt (9:1))=0.3

NMR $^1$H (400 MHz, CDCl$_3$) δ (ppm): 8.00 (s, 1H, NH); 7.62 (d, 1H, $^4$J=2.7 Hz, H$_7$); 7.44 (dd, 1H, $^3$J=8.8 Hz, 17.8 Hz, H$_9$); 6.86 (d, 1H, $^3$J=8.8 Hz, H$_4$); 5.72 (dd, 1H, $^2$J$_{gem}$=1.4 Hz, $^3$J$_{trans}$=17.8 Hz, H$_{10a}$); 5.28 (dd, 1H, $^2$J$_{gem}$=1.4 Hz, $^3$J$_{cis}$=11.2 Hz, H$_{10b}$); 4.52 (sept., 1H, $^3$J=6.1 Hz, H$_2$); 1.34 (d, 6H, $^3$J=6.1 Hz, H$_1$)

NMR $^{19}$F (376.5 MHz, CDCl$_3$) δ (ppm): −70.1 (s, 2F, F$_{11}$); −118.6 (s, 2F, F$_{12}$)

NMR $^{13}$C (100 MHz, CDCl$_3$) δ (ppm): 155.7 (C=O); 153.3 (C3); 130.9 (C9); 128.6 (C8); 128.1 (C6); 124.8 (CF$_2$CO); 121.2 (C5); 119.0 (C4); 115.2 (C10); 114.2 (C7); 108.1 (CF$_2$Cl); 71.3 (C2); 22.0 (C1)

2$^{nd}$ step: synthesis of ruthenium complexes 1a, 1b, 1c, 1d, 1e, 1f, 11 and 12 from amides 6a, 6b, 6c, 6d, 6f, 10b According to a general procedure, the amide ligand (1 eq.), copper chloride (I) (1 eq) and the indenylidene precatalyst (1 eq.) are introduced into a round-bottom flask under argon. Anhydrous dichloromethane (2-3 mL) is added to it. The reaction medium is then degassed three times, placed at 30-33° C. under an argon atmosphere and kept under agitation for around 5 hours.

The raw reaction material is then concentrated under vacuum. The residue is combined with acetone (1-2 mL) and filtered on Celite. The filtrate is concentrated under vacuum and the residue is purified by chromatography on silica gel.

Synthesis of the Ruthenium Complex 1a

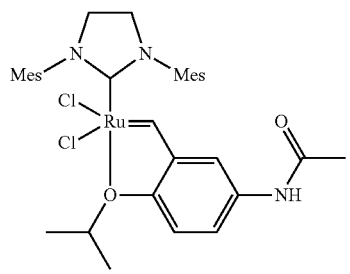

Using the general procedure for obtaining ruthenium complexes with N-(4-isopropoxy-3-vinylphenyl)acetamide 6a (24 mg; 0.011 mmol), the complex 1a is obtained after chromatography on silica gel (eluent: EP/Acetone (1:1)) in the form of a green solid (73 mg; 98%).

Rf (EP/Acetone (1:1))=0.52

NMR $^1$H (400 MHz, (CD$_3$)$_2$CO) δ (ppm): 16.42 (s, 1H, H$_9$); 10.23 (s, 1H, NH); 7.78 (d, 1H, $^3$J=8.6 Hz, H$_5$); 7.55 (s, 1H, H$_7$); 7.05 (s, 4H, H$_{12}$); 6.91 (d, 1H, $^3$J=8.6 Hz, H$_4$); 4.88 (sept., 1H, $^3$J=6.1 Hz, H$_2$); 4.24 (s, 4H, H$_{10}$); 2.45 (m, 18H, H$_{11}$, H$_{13}$); 2.09 (s, 3H, H$_{14}$); 1.22 (d, 6H, $^3$J=6.1 Hz, H$_1$)

Synthesis of the Ruthenium Complex 1b

Using the general procedure for obtaining ruthenium complexes with N-(4-isopropoxy-3-vinylphenyl)trifluoroacetamide 6b (11.7 mg; 0.04 mmol), complex 1b is obtained after chromatography on silica gel (eluent: EP/Acetone (7:3)) in the form of a green solid (26.1 mg; 88%).

Rf (EP/Acetone (3:2))=0.37

NMR $^{19}$F (376.5 MHz, (CD$_3$)$_2$CO) δ (ppm): −76.5 (s, 3F, F$_{14}$)

NMR $^1$H (400 MHz, (CD$_3$)$_2$CO) δ (ppm): 16.40 (s, 1H, H$_9$); 9.24 (s, 1H, NH); 7.64 (dd, 1H, $^3$J=8.6 Hz, $^4$J=2.8 Hz, H$_5$); 7.55 (d, 1H, $^4$J=2.8 Hz, H$_7$); 7.05 (s, 4H, H$_{12}$); 7.01 (d, 1H, $^3$J=8.6 Hz, H$_4$); 4.95 (sept., 1H, $^3$J=6.1 Hz, H$_2$); 4.27 (s, 4H, H$_{10}$); 2.43 (m, 18H, H$_{11}$, H$_{13}$); 1.22 (d, 6H $^3$J=6.1 Hz, H$_1$)

Synthesis of the Du Ruthenium Complex 1c

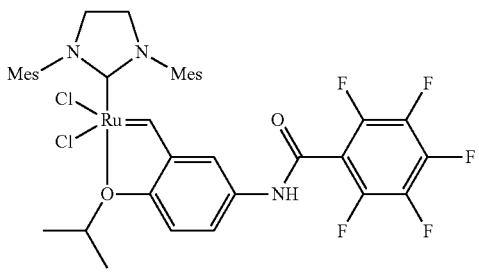

Using the general procedure for obtaining ruthenium complexes with N-(4-isopropoxy-3-vinylphenyl)pentafluorobenzamide 6c (9 mg; 0.02 mmol), complex 1c is obtained after chromatography on silica gel (eluent: EP/Acetone (7:3)) in the form of a green solid (10 mg; 50%).

Rf (EP/Acetone (7:3))=0.41

NMR $^{19}$F (376.5 MHz, $(CD_3)_2CO$) δ (ppm): −143.6 (d, 2F, $^3J_{F\text{-}F}$=15 Hz, $F_{15}$); −155.2 (t, 1F, $^3J_{F\text{-}F}$=20 Hz, $F_{17}$); −16.5 (dt, 2F, $^3J_{F\text{-}F}$=20 Hz, $^3J_{F\text{-}F}$=15 Hz, $F_{16}$)

NMR $^1$H (400 MHz, $(CD_3)_2CO$) δ (ppm): 16.41 (s, 1H, $H_9$); 10.35 (s, 1H, NH); 7.75 (dd, 1H, $^3J$=8.6 Hz, $^4J$=2.8 Hz, $H_5$); 7.67 (d, 1H, $^4J$=2.8 Hz, $H_7$); 7.07 (s, 4H, $H_{12}$); 7.03 (d, 1H, $^3J$=8.6 Hz, $H_4$); 4.95 (sept., 1H, $^3J$=6.1 Hz, $H_2$); 4.27 (s, 4H, $H_{10}$); 2.43 (m, 18H, $H_{11}$, $H_{13}$); 1.22 (d, 6H, $^3J$=6.1 Hz, $H_1$)

Synthesis of the Ruthenium Complex 1d

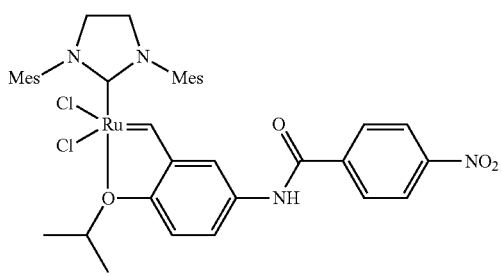

Using the general procedure for obtaining ruthenium complexes with N-(4-isopropoxy-3-vinylphenyl)/paranitrobenzamide 6d (8 mg; 0.02 mmol), complex 1d is obtained after chromatography on silica gel (eluent: EP/Acetone (6:4)) in the form of a green solid (18 mg; 95%).

Rf (EP/Acetone (7:3))=0.34

NMR $^1$H (400 MHz, $(CD_3)_2CO$) δ (ppm): 16.46 (s, 1H, $H_9$); 9.97 (s, 1H, NH); 8.36 (d, 2H, $^3J$=8.8 Hz, $H_{15}$); 8.21 (d, 2H, $^3J$=8.8 Hz, $H_{16}$); 7.85 (dd, 1H, $^3J$=8.6 Hz, $^4J$=2.8 Hz, $H_5$); 7.74 (d, 1H, $^4J$=2.8 Hz, $H_7$); 7.07 (s, 4H, $H_{12}$); 7.02 (d, 1H, $^3J$=8.6 Hz, $H_4$); 4.95 (sept., 1H, $^3J$=6.1 Hz, $H_2$); 4.27 (s, 4H, $H_{10}$); 2.43 (m, 18H, $H_{11}$, $H_{13}$); 1.24 (d, 6H, $^3J$=6.1 Hz, $H_1$)

Synthesis of the Ruthenium Complex 1e

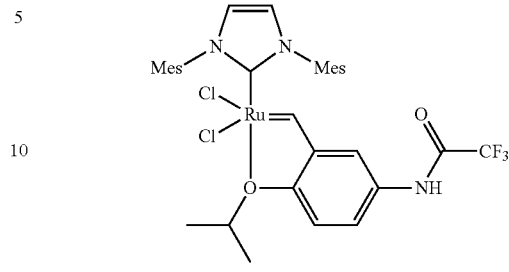

The N-(4-isopropoxy-3-vinylphenyl)trifluoro-acetamide ligand 6b (22 mg; 0.08 mmol; 1 eq.), copper chloride (I) (8 mg, 1 eq) and the $2^{nd}$ generation Nolan precatalyst (68 mg, 1 eq.) of formula 2c are introduced into a round-bottom flask under argon. Anhydrous dichloromethane (3 mL) is added to it. The reaction medium is then degassed three times, placed at 30-33° C. under an argon atmosphere and kept under agitation for around 5 hours.

The raw reaction material is then concentrated under vacuum. The residue is combined with acetone (1-2 mL) and filtered on Celite. The filtrate is concentrated under a vacuum and the residue is purified by chromatography on silica gel.

The complex 1e is obtained after chromatography on silica gel (eluent: EP/Acetone (4:1)) in the form of a green solid (52 mg; 88%). Rf (EP/Acetone (1:1))=0.13

NMR $^{19}$F (376.5 MHz, $(CD_3)_2CO$) δ (ppm): −76.5 (s, 3F, $F_{14}$)

NMR $^1$H (400 MHz, $(CD_3)_2CO$) δ (ppm): 16.54 (s, 1H, $H_9$); 10.44 (s, 1H, NH); 7.79 (dd, 1H, $^3J$=8.6 Hz, $^4J$=2.6 Hz, $H_5$); 7.68 (d, 1H, $^4J$=2.6 Hz, $H_7$); 7.48 (s, 2H, $H_{10}$); 7.14 (s, 4H, $H_{12}$); 7.09 (m, 1H, $H_4$); 4.99 (sept., 1H, $^3J$=6.1 Hz, $H_2$); 2.47 (s, 6H, $H_{17}$); 2.24 (s, 12H, $H_{11}$); 1.31 (d, 6H, $^3J$=6.1 Hz, $H_1$)

Synthesis of the Ruthenium Complex 1f

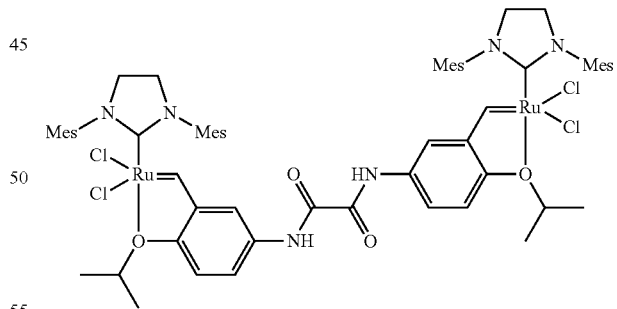

The N,N'-bis(4-isopropoxy-3-vinylphenyl)oxamide ligand 6f (8 mg; 0.02 mmol; 1 eq.), copper chloride (I) (4 mg, 2.1 eq) and the indenylidene precatalyst (37 mg, 2.1 eq.) are introduced into a round-bottom flask under argon. Anhydrous dichloromethane (5 mL) is added to it. The reaction medium is then degassed three times, placed at 30-33° C. under an argon vacuum and kept under agitation for around 5 hours.

The raw reaction material is then concentrated under vacuum. The residue is combined with acetone (2 mL) and filtered on frit. The complex 1f is thus isolated in the form of a green solid (15 mg; 59%).

NMR $^1$H (400 MHz, CD$_2$Cl$_2$) δ (ppm): 16.36 (s, 2H, H$_9$); 9.30 (s, 2H, NH); 7.89 (d, 2H, $^3$J=7.8 Hz, H$_5$); 7.35 (s, 2H, H$_7$); 7.09 (s, 8H, H$_{12}$); 6.84 (d, 2H, $^3$J=8.0 Hz, H$_4$); 4.86 (m, 2H, H$_2$); 4.16 (5, 8H, H$_{10}$); 1.86 (m, 36H, H$_{11}$, H$_{13}$); 1.23 (d, 12H, $^3$J=6.1 Hz, H$_1$)

Synthesis of the Marked Ruthenium Complex 11

Once the trifluoroacetamide function is clearly identified as the function most capable of activating the precatalyst, the introduction of an ion pattern (ion tag) can then be performed.

For this, the invention proposes substituting the chlorine atom of compound 10a with a tertiary amine (imidazole, pyridine, etc.).

Thus, the inventors performed the substitution with pyridine on 4-chloro-N-(4-isopropoxy-3-vinylphenyl)butanamide 10a in order to easily produce the desired ion ligand 10b. The complexing thereof with the Grubbs II catalyst leads to complex 11.

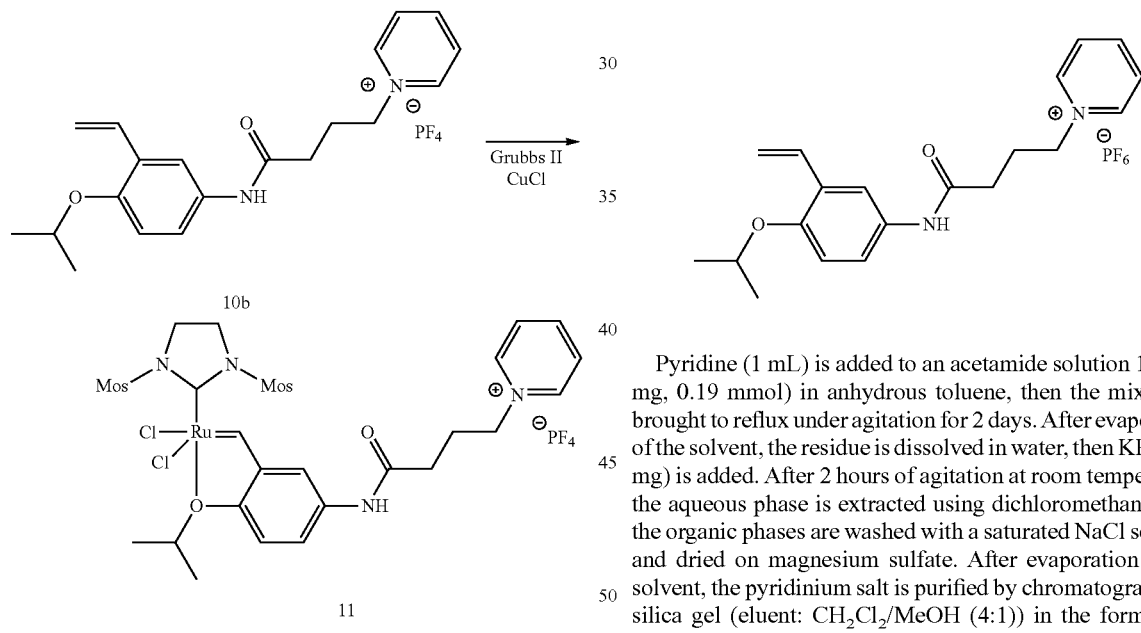

Synthesis of the 4-chloro-N-(4-isopropoxy-3-vinylphenyl)butanamide compound 10a

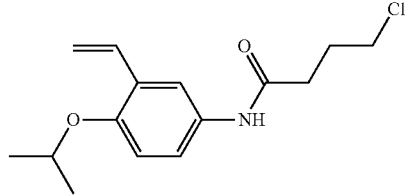 [SMILES: C=Cc1cc(NC(=O)CCCCl)ccc1OC(C)C]

Using the general procedure for obtaining amides from 4-isopropoxy-3-vinylaniline 5 (50 mg; 0.3 mmol) and with 3-chloropropanoyl chloride (15 μL), acetamide is obtained after chromatography on silica gel (eluent: CH$_2$Cl$_2$) in the form of a pink solid (52 mg, 65%).

Rf (CH$_2$Cl$_2$)=0.3

NMR $^1$H (400 MHz, CDCl$_3$) δ (ppm): 7.81 (s, 1H, NH); 7.54 (d, 1H, $^4$J=2.7 Hz, H$_7$); 7.34 (dd, 1H, $^3$J=8.8 Hz, $^4$J=2.7 Hz, H$_5$); 6.98 (dd, 1H, $^3$J$_{cis}$=11.2 Hz, $^3$J$_{trans}$=17.8 Hz, H$_9$); 6.79 (d, 1H, $^3$J=8.8 Hz, H$_4$); 5.67 (dd, 1H, $^2$J$_{gem}$=1.4 Hz, $^3$J$_{trans}$=17.8 Hz, H$_{10a}$); 5.21 (dd, 1H, $^2$J$_{gem}$=1.4 Hz, $^3$J$_{cis}$=11.2 Hz, H$_{10b}$); 4.44 (sept., 1H, $^3$J=6.1 Hz, H$_2$); 3.60 (t, 2H, $^3$J=7.1 Hz, CH$_2$Cl); 2.48 (t, 2H, $^3$J=7.1 Hz, H$_{12}$); 2.14 (m, 2H, H$_{11}$); 1.31 (d, 6H, $^3$J=6.1 Hz, H$_1$)

NMR $^{13}$C (100 MHz, CDCl$_3$) δ (ppm): 170.1 (C=O); 152.0 (C3); 131.3 (C9); 130.8 (C8); 128.3 (C6); 121.1 (C7); 118.6 (C5); 115.0 (C4); 114.5 (C10); 71.4 (C2); 44.4 (C13); 33.8 (C12); 27.9 (C11); 22.0 (Cl)

Synthesis of the 1-(4-(4-isopropoxy-3-vinylphenylamino)-4-oxobutyl)pyridinium hexafluorophosphate (V) compound 10b

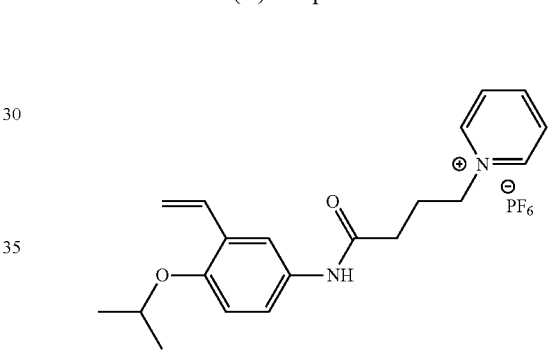

Pyridine (1 mL) is added to an acetamide solution 10a (52 mg, 0.19 mmol) in anhydrous toluene, then the mixture is brought to reflux under agitation for 2 days. After evaporation of the solvent, the residue is dissolved in water, then KPF$_6$ (38 mg) is added. After 2 hours of agitation at room temperature, the aqueous phase is extracted using dichloromethane, then the organic phases are washed with a saturated NaCl solution and dried on magnesium sulfate. After evaporation of the solvent, the pyridinium salt is purified by chromatography on silica gel (eluent: CH$_2$Cl$_2$/MeOH (4:1)) in the form of an amorphous solid (38 mg, 44%).

Rf (CH$_2$Cl$_2$/MeOH (8:2))=0.2

NMR $^1$H (400 MHz, MeOD) δ (ppm): 8.98 (d, 2H, $^3$J=Hz, H$_{14}$); 8.54 (dd, 1H, $^3$J=Hz, H$_{16}$); 8.06 (t, 2H, $^3$J=Hz, H$_{15}$); 7.62 (d, 1H, $^4$J=2.7 Hz, H$_7$); 7.30 (dd, 1H, $^3$J=8.8 Hz, $^4$J=2.7 Hz, H$_5$); 6.97 (dd, 1H, $^3$J$_{cis}$=11.2 Hz, $^3$J$_{trans}$=17.8 Hz, H$_9$); 6.88 (d, 1H, $^3$J=8.8 Hz, H$_4$); 5.70 (dd, 1H, $^2$J$_{gem}$=1.4 Hz, $^3$J$_{trans}$=17.8 Hz, H$_{10a}$); 5.20 (dd, 1H, $^2$J$_{gem}$=1.4 Hz, $^3$J$_{cis}$=11.2 Hz, H$_{10b}$); 4.69 (t, 2H, $^3$J=7.1 Hz, CH$_2$Pyr); 4.57 (s, 1H, NH); 4.50 (sept., 1H, $^3$J=6.1 Hz, H$_2$); 2.50 (t, 2H, $^3$J=7.1 Hz, H$_{12}$); 2.38 (m, 2H, H$_{11}$); 1.31 (d, 6H, $^3$J=6.1 Hz, H$_1$)

NMR $^{13}$C (100 MHz, CDCl$_3$) δ (ppm): 171.9 (C=O); 153.2 (C3); 147.0 (C14); 146.0 (C16); 132.8; 132.7; 129.5; 129.3; 122.4; 119.58; 116.2; 114.6; 72.5; 62.5; 33.4; 27.9; 22.4

Synthesis of the Ruthenium Complex 11

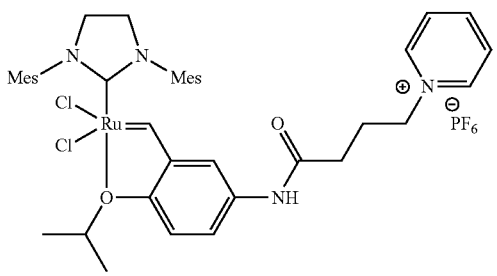

The 1-(4-(4-isopropoxy-3-vinylphenylamino)-4-oxobutyl)pyridinium hexafluorophosphate(V) ligand 10b (5 mg; 0.011 mmol; 1 eq.), copper chloride (I) (2 mg, 1 eq.) and the indenylidene precatalyst (9.6 mg, 1 eq.) are introduced into a round-bottom flask under argon. Anhydrous dichloromethane (3 mL) is added to it. The reaction medium is then degassed three times, placed at 30-33° C. under an argon atmosphere and kept under agitation for around 5 hours.

The raw reaction material is then concentrated under vacuum. The residue is combined with acetone (2 mL) and filtered on frit. The complex 11 is thus isolated in the form of an amorphous dark green solid.

NMR $^1$H (400 MHz, (CD$_3$)$_2$CO) δ (ppm): 16.40 (s, 1H, H$_9$); 9.25 (d, 2H, $^3$J=5.8 Hz, H$_{17}$); 9.18 (s, 2H, NH); 8.76 (t, 1H, $^3$J=6.5 Hz, H$_{19}$); 8.32 (d, 2H, $^3$J=6.5 Hz, H$_{18}$); 7.62 (m, 2H, H$_5$); 7.50 (d, 1H, $^3$J=2.5 Hz, H$_7$); 7.06 (s, 4H, H$_{12}$); 6.94 (d, 1H, $^3$J=8.8 Hz, H$_4$); 5.00 (t, 2H, $^3$J=7.1 Hz, H$_{18}$); 4.90 (m, 1H, H$_2$); 4.27 (s, 4H, H$_{10}$); 2.59 (m, 4H, H$_{14}$, H$_{18}$); 2.44 (m, 18H, H$_{11}$ H$_{13}$); 1.23 (d, 6H, $^3$J=6.1 Hz, H$_1$)

In the second part, the activation of the activated ruthenium complexes 1a, 1b, 1c, 1d, 1e and 1f was studied.

Complexes 1a, 1b, 1c, 1d according to the invention and the Hoveyda complex 3b of the prior art were studied in an olefin cyclization metathesis reaction with diethylmalonate metallyl-allyl 7 at room temperature in dichloromethane in the presence of 1 mol % of complex according to the following reaction diagram.

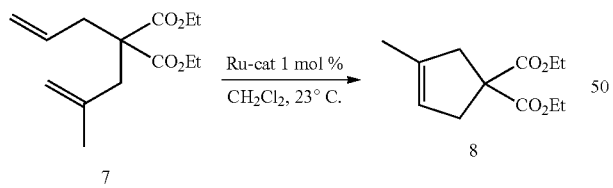

The results of the conversion rates obtained with these compounds are shown in the graph of FIG. 1.

These results clearly show the acetamide function activating effect.

In particular, when this acetamide function has a trifluoromethyl group (complex 1b), a conversion rate of over 37% after only 15 minutes of reaction is obtained, by comparison with 5% in the case of the Hoveyda complex 3b.

The activity of compound 1e (resulting from the complexing with the Nolan catalyst 2c) and of compound 1b (resulting from the complexing with the Grubbs II catalyst 2b), on one hand, and that of the complex of the Hoveyda prior art complex 3b, on the other hand, were also studied in the same reaction and under the same reaction conditions.

Figure 2:
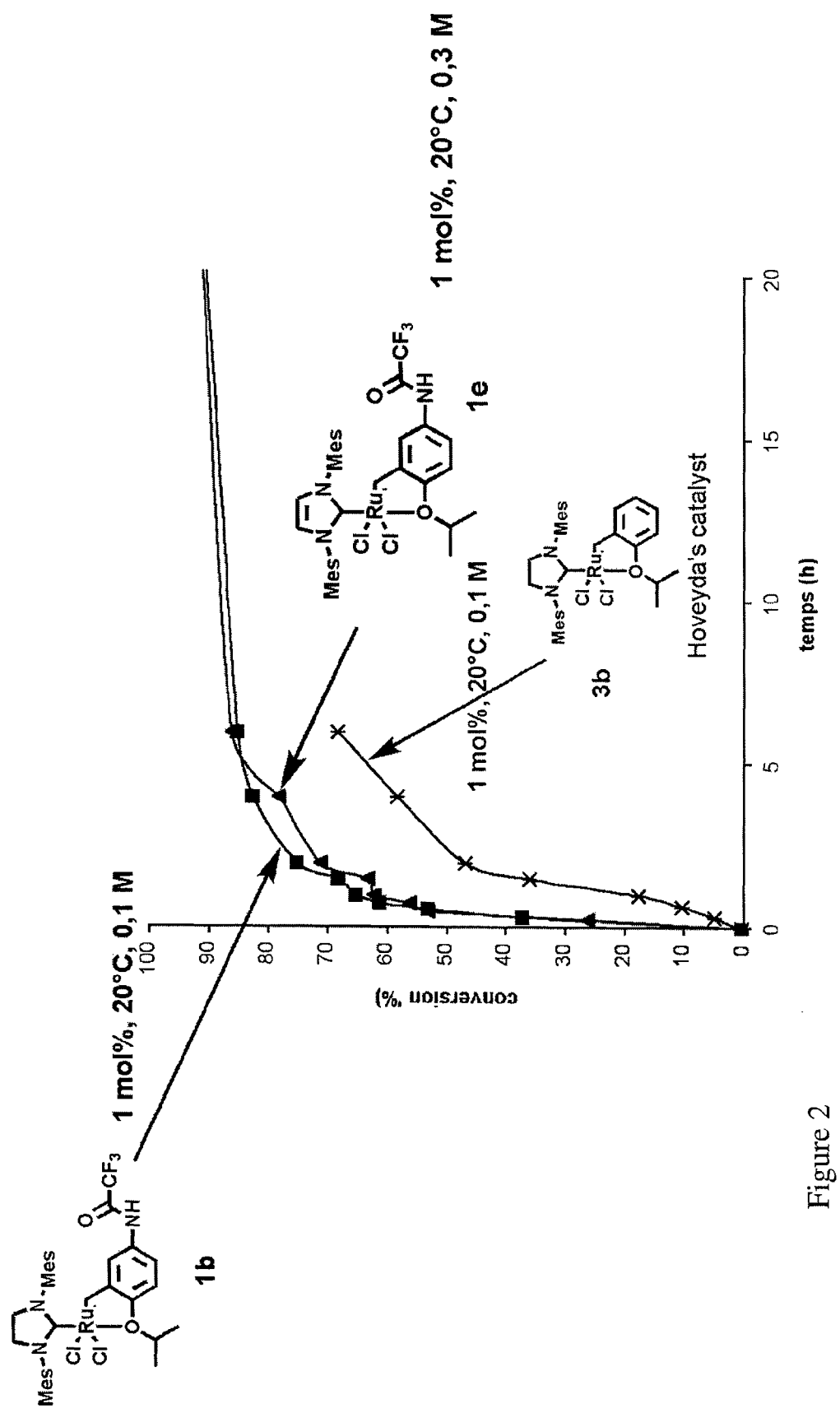
FIG. 2 is a graph showing the conversion rate over time of a metallyl-allyl diethyl malonate compound in the context of a metathesis cyclization reaction at room temperature, in the presence of 1 mol % of the Hoveyda complex 3b on one hand and in the presence of 1 mol % of catalytic complexes according to the invention 1b and 1e on the other hand.
Figure 3:
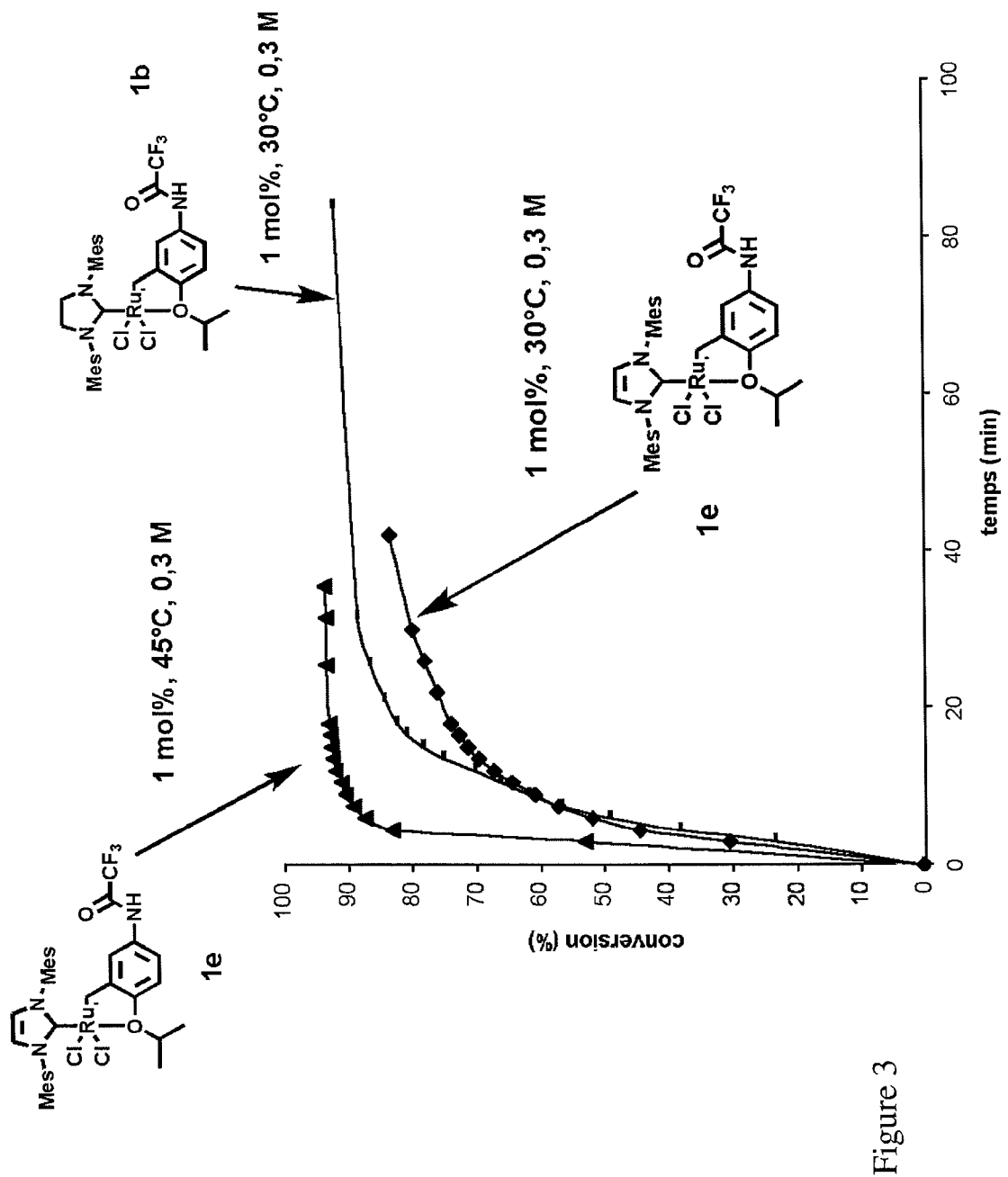
FIG. 3 is a graph showing the conversion rate over time of a metallyl-allyl diethyl malonate compound in the context of a metathesis cyclization reaction at 45° C., in the presence of 1 mol % of the catalytic complex according to the invention 1e.

The results of the conversion rates obtained with these compounds are shown in the graph according to FIG. 2.

Very surprisingly, these results show a similar activity for catalysts 1e and 1b, whereas the Grubbs complex II 2b (bearing a SIMes ligand) is much more active than the Nolan complex 2c (bearing an IMes ligand). This result is very beneficial because the catalytic species bearing an IMes ligand (resulting from the Nolan complex 2c) is much more thermically stable than the catalytic species bearing a SIMes ligand (generated by the Grubbs II complex 2b).

The invention therefore offers the possibility of performing olefin metathesis reactions under more drastic conditions (higher heat) with the activated complex 1e when the substrates are very bulky (for example tetrasubstituted olefins). Thus a metathesis cyclization reaction of a metallyl-allyl diethyl malonate compound takes place at 45° C., in the presence of 1 mol % of the catalytic complex 1e on one hand and at 30° C. in the presence of 1 mol % of the catalytic complexes 1b and 1e on the other hand. The results of the conversion rates obtained with these compounds are shown in the graph according to FIG. 3. As expected, the activated IMes catalyst 1e shows a remarkable activity with a conversion rate of 87% after only 6 minutes of reaction.

Figure 4:
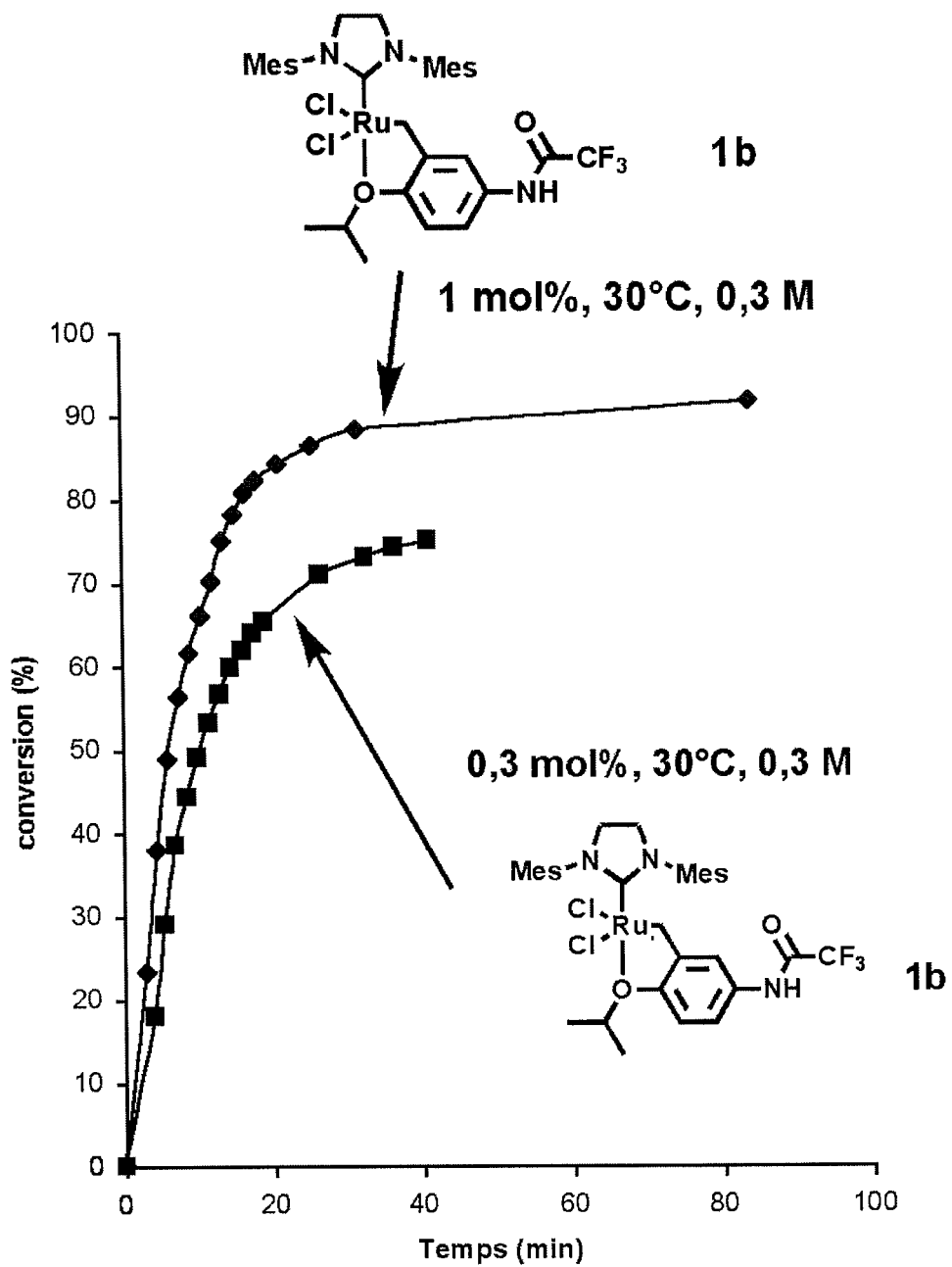
FIG. 4 is a graph showing the conversion rate over time of a metallyl-allyl diethyl malonate compound in the context of a metathesis cyclization reaction at 30° C., in the presence of 1 mol % of the catalytic complex according to the invention 1b on one hand and in the presence of 0.3 mol % of the catalytic complex according to the invention 1b on the other hand.

The activity of the activated complex 1b, by reducing its catalytic load in the metathesis cyclization reaction of a metallyl-allyl diethyl malonate compound was also evaluated. FIG. 4 is a graph showing the conversion rate over time of a metallyl-allyl diethyl malonate in the context of a metathesis cyclization reaction at 30° C., in the presence of 1 mol % of the catalytic complex according to the invention 1b and 0.3 mol % of the catalytic complex according to the invention 1b. The graph shows a slight decrease in reactivity; however, it remains remarkable since 75% of the conversion is observed after only 40 minutes of reaction.

Figure 5:
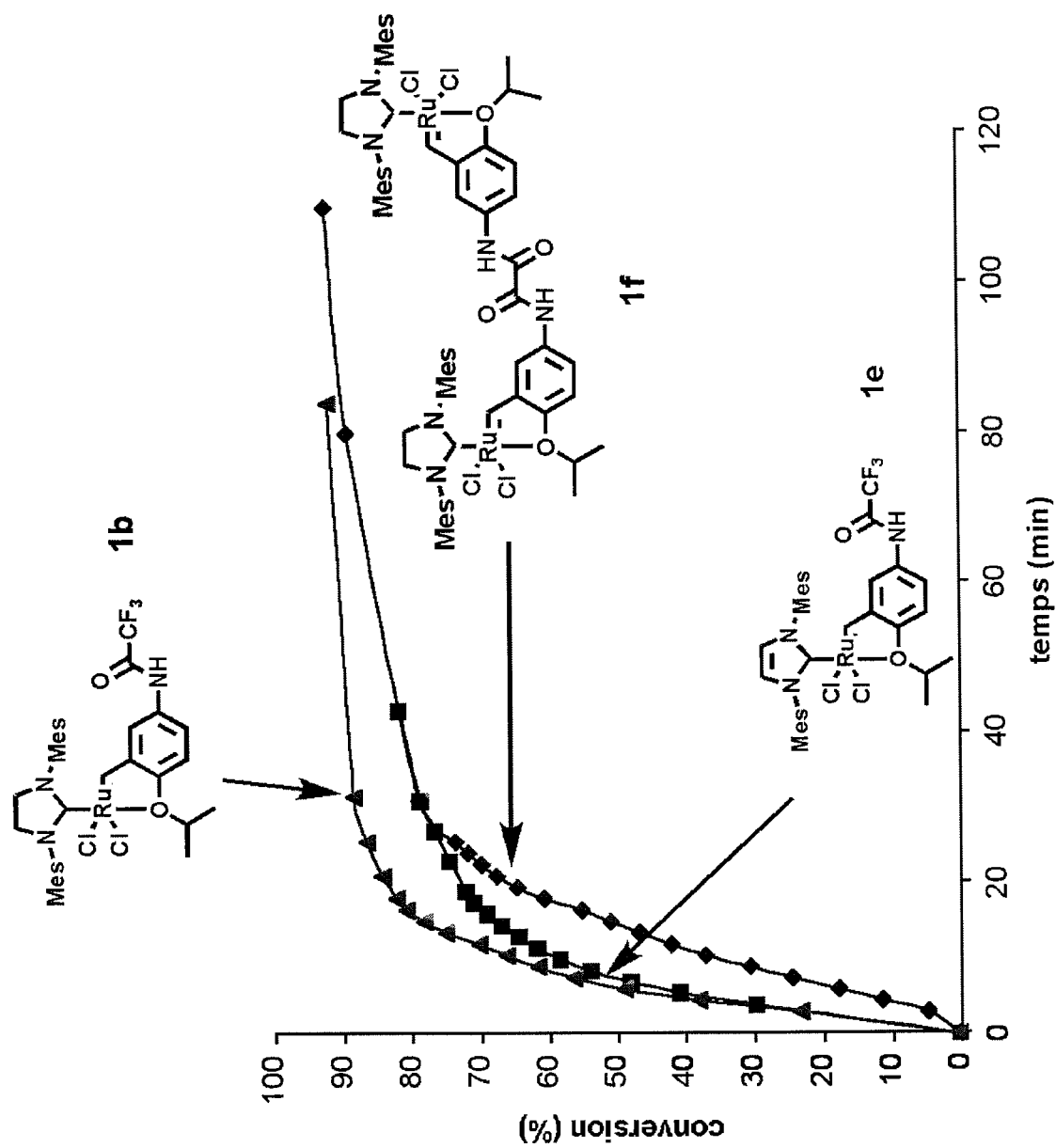
FIG. 5 is a graph showing the conversion rate over time of a metallyl-allyl diethyl malonate compound in the context of a metathesis cyclization reaction at 30° C., in the presence of 1 mol % of the catalytic complex according to the invention 1b, 1e and 1f.
Figure 6:
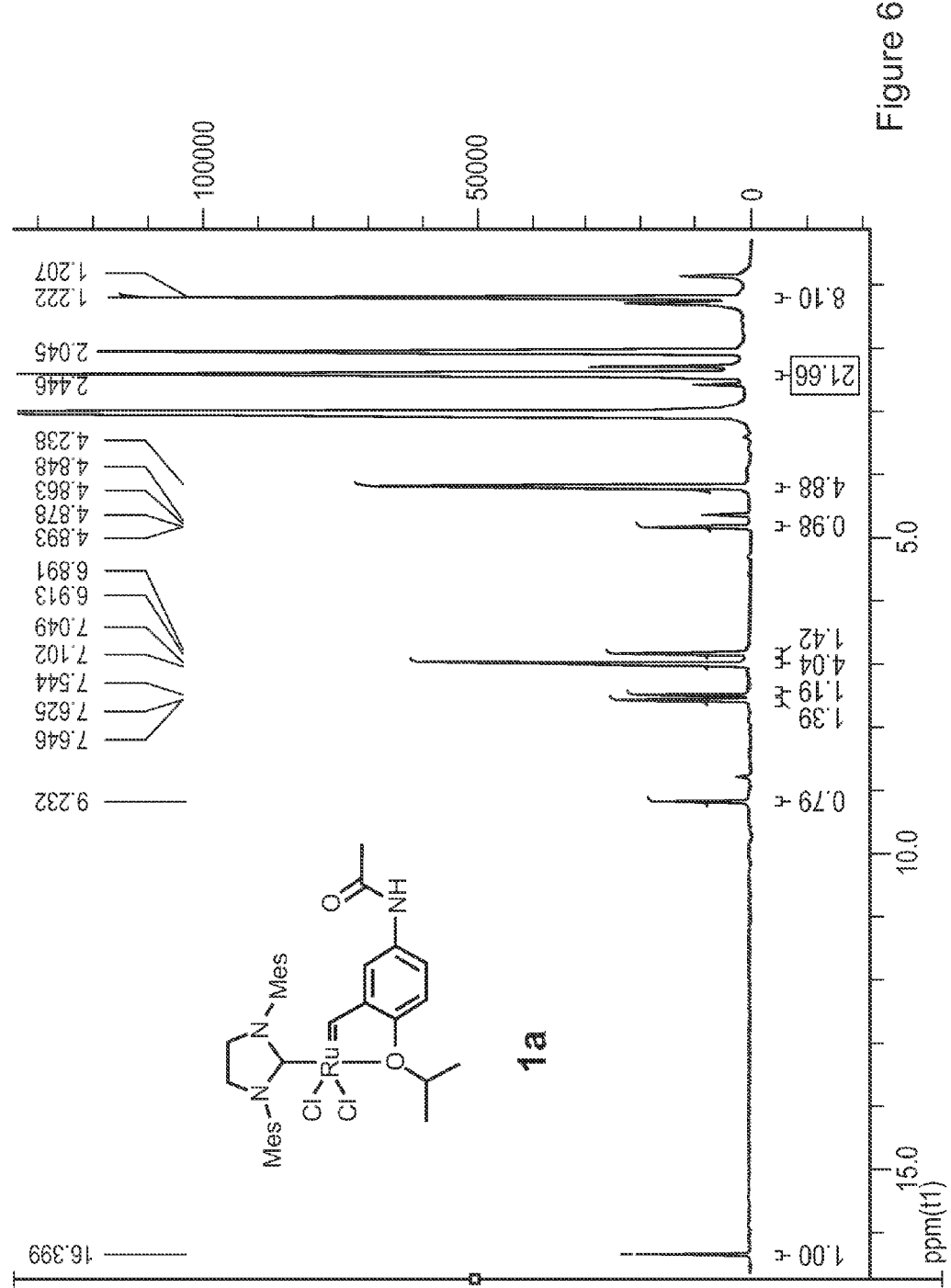
FIGS. 6 to 11 show the NMR spectra of various examples of ruthenium complexes 1a, 1b, 1c, 1d, 1e and 1f.
Figure 7:
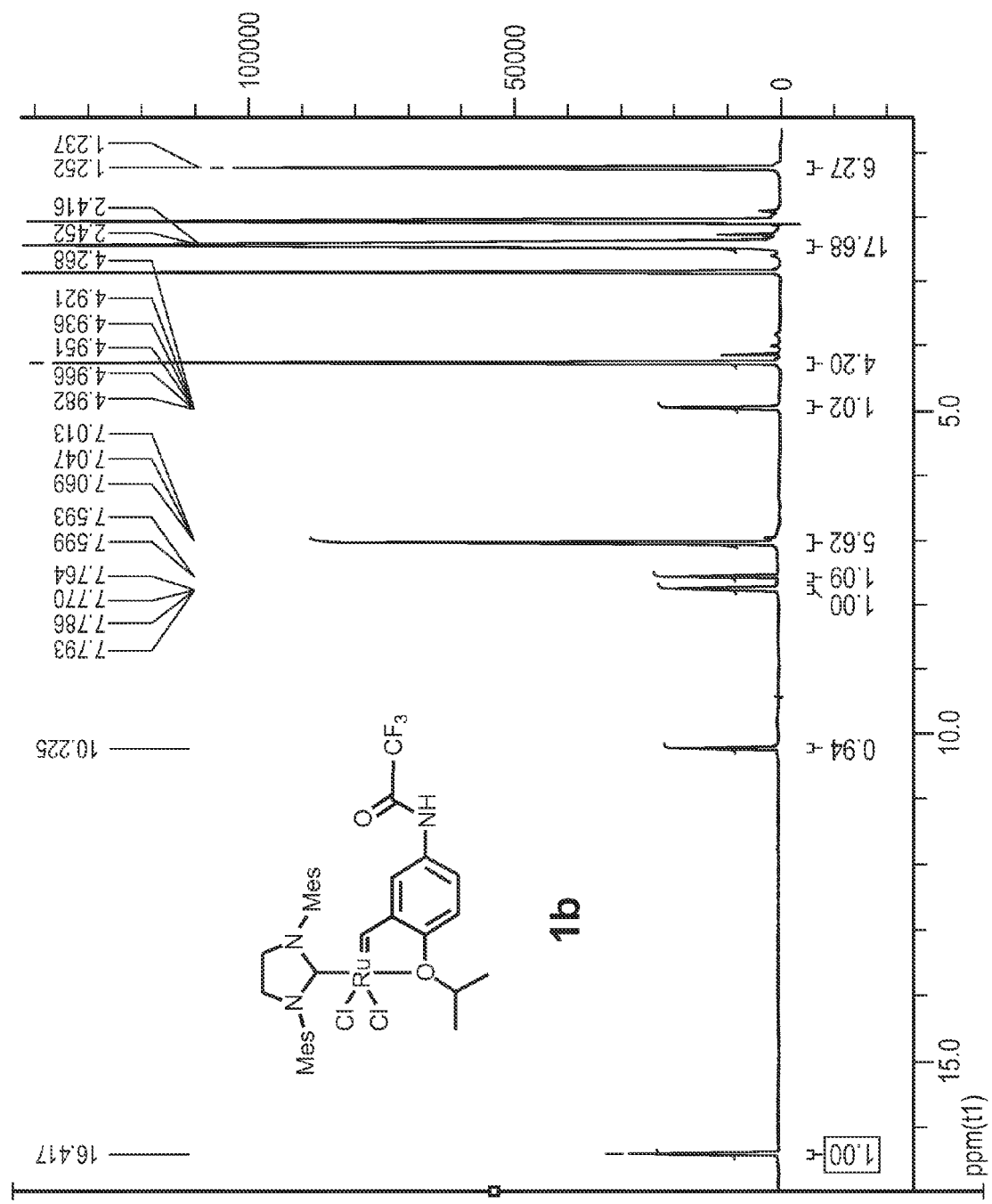
Figure 8:
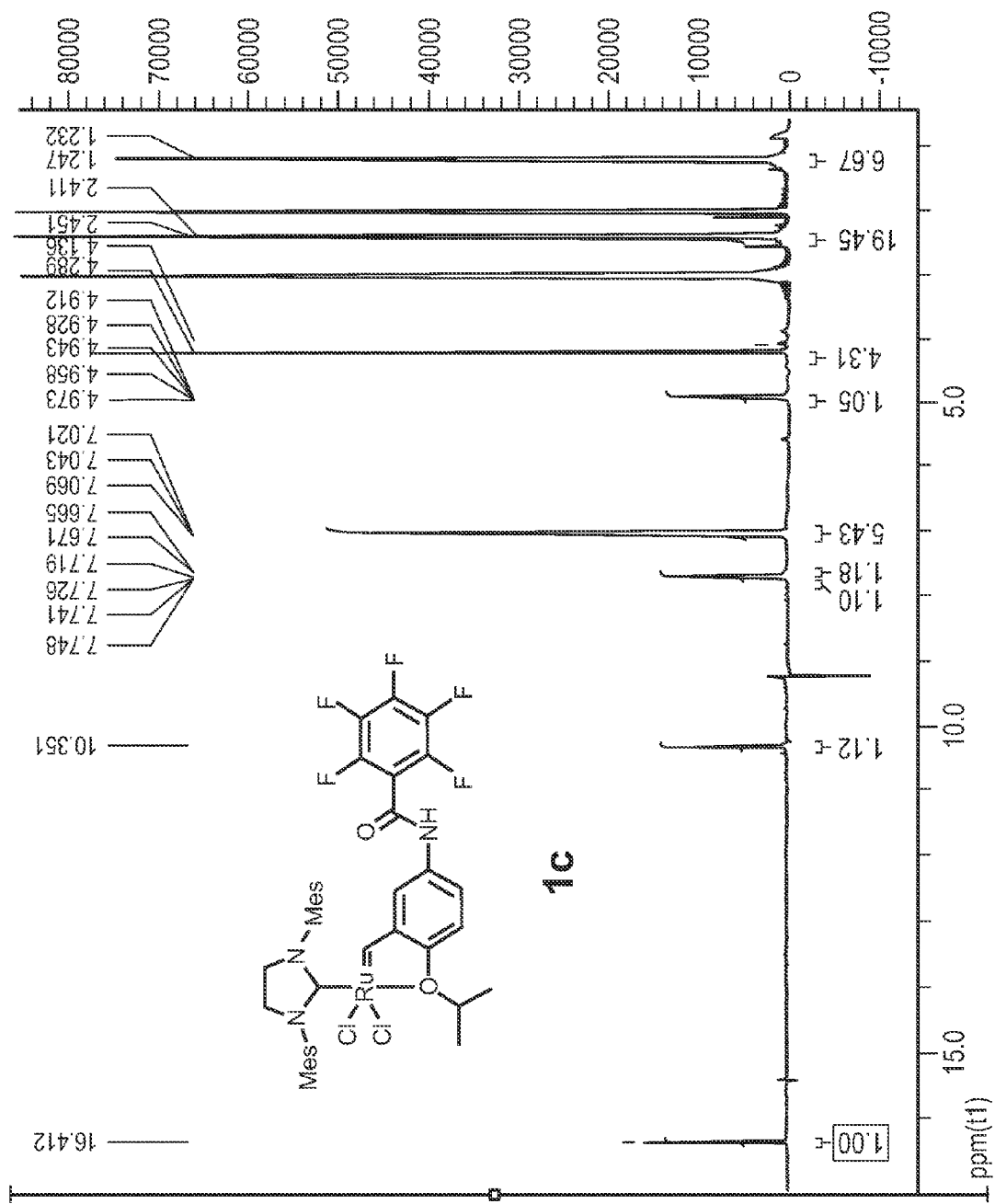
Figure 9:
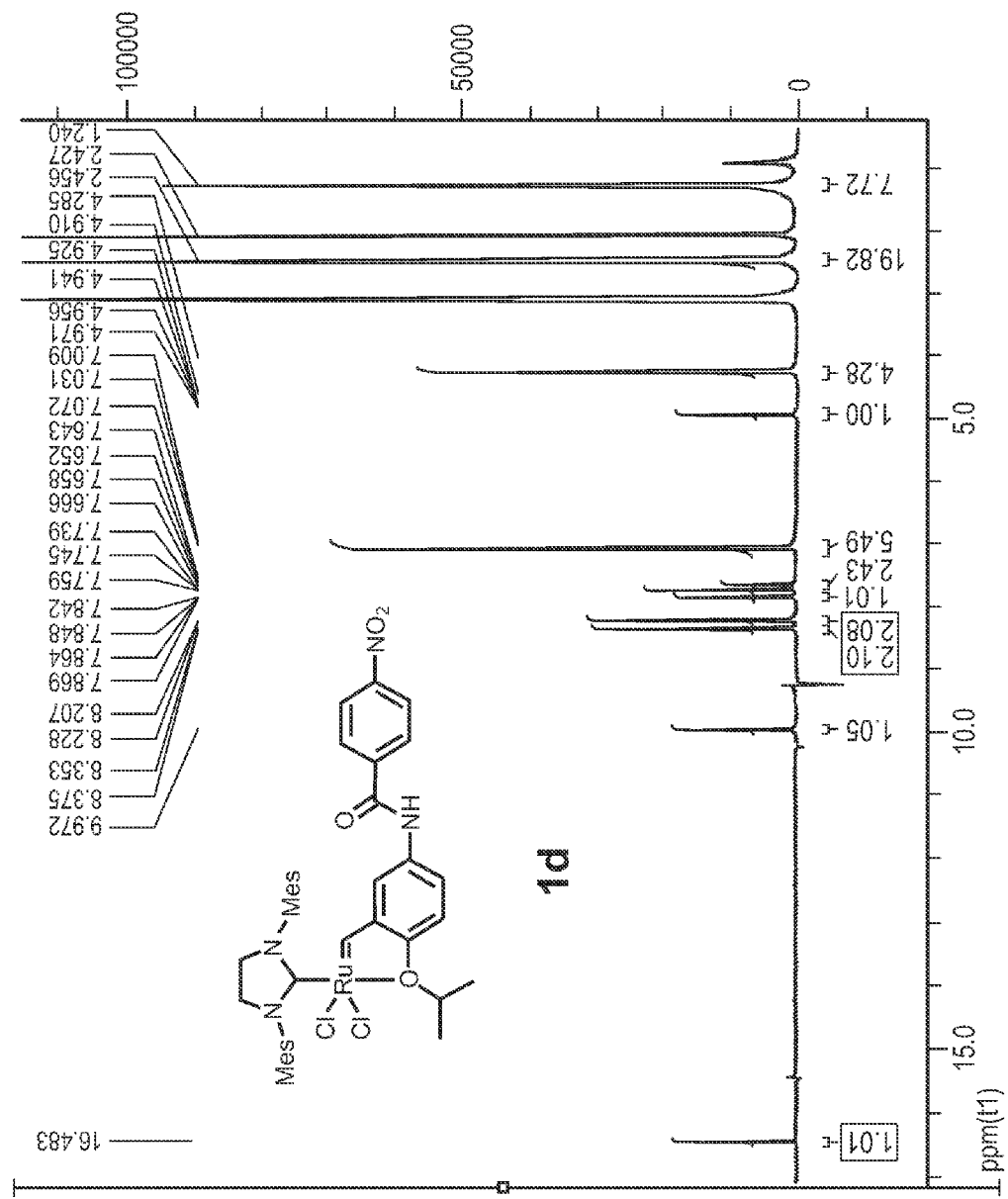
Figure 10:
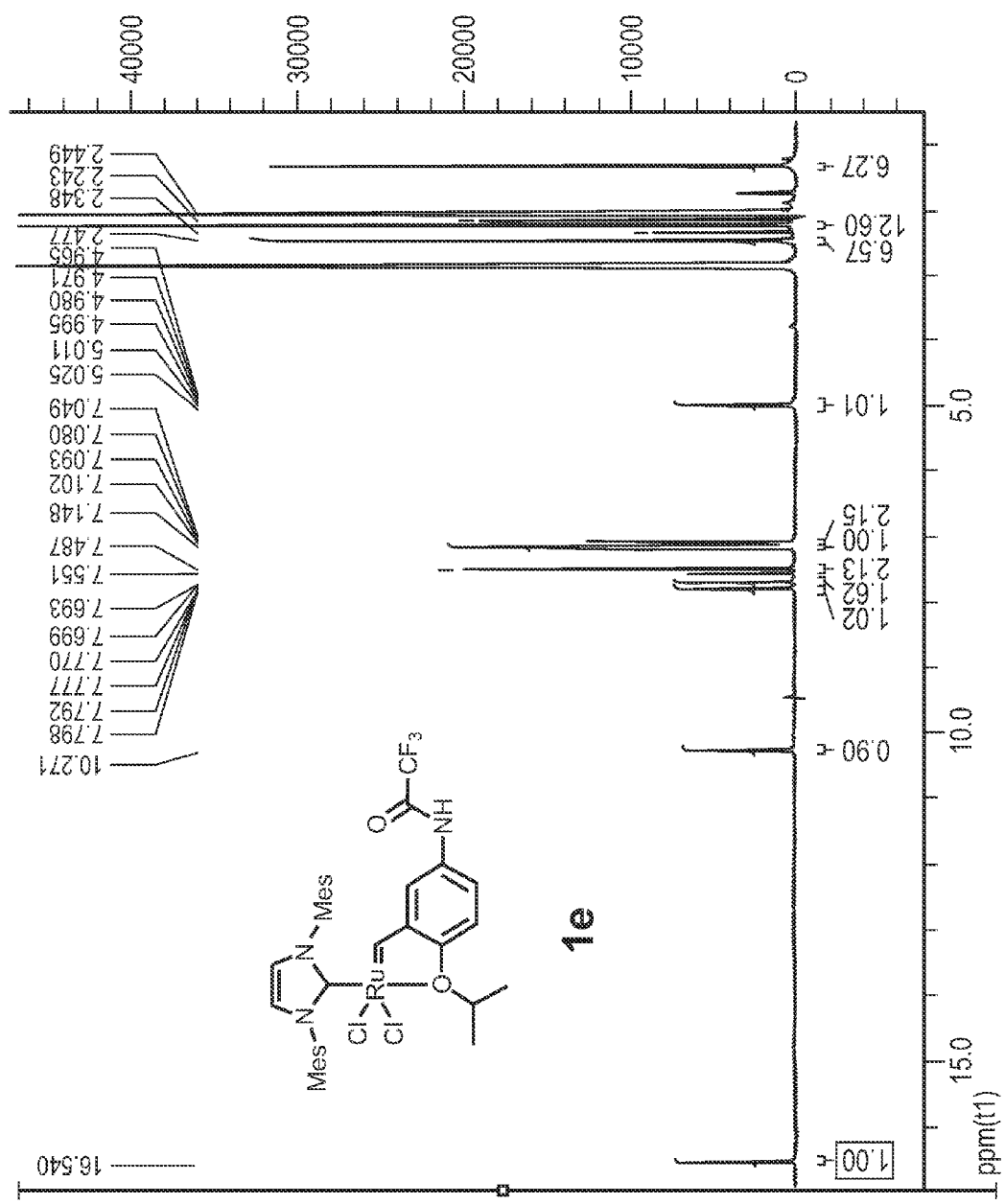
Figure 11:
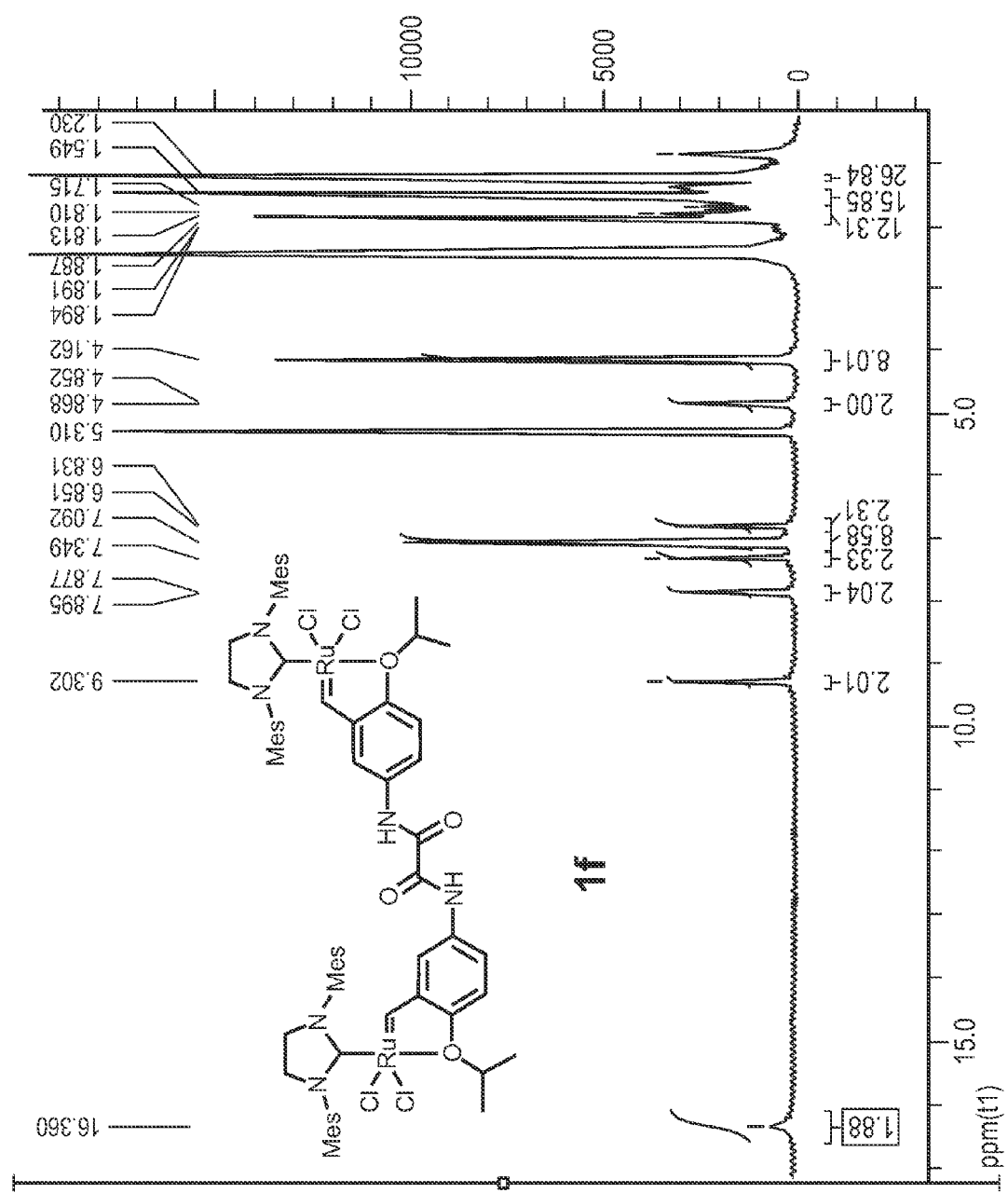

Finally, the activated dimer complex 1f was also evaluated and its activity was compared with the activated complexes 1b and 1e. FIG. 5 is a graph showing the conversion rate over time of a metallyl-allyl diethylmalonate compound in the context of a metathesis cyclization reaction at 30° C., in the presence of 1 mol % of the catalytic complexes according to the invention 1b, 1e and 1f.

What is claimed is:

1. A compound of formula (I) for catalysis:

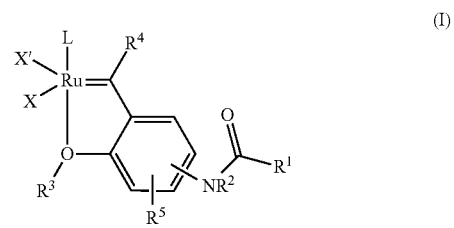

in which:

L is a neutral ligand;

X, X' are anionic ligands;

$R^1$ and $R^2$ are, independently, a hydrogen, a $C_1$ to $C_6$ alkyl, a $C_1$ to $C_6$ perhalogenoalkyl, an aldehyde, a ketone, an ester, an amide, a nitrile, an optionally substituted aryl, a pyridinium alkyl, a pyridinium perhalogenoalkyl or an optionally substituted $C_5$ or $C_6$ cyclohexyl, a $C_nH_{2n}Y$ or $C_nF_{2n}Y$ radical with n being between 1 and 6 and Y being an ion marker, or a radical of formula:

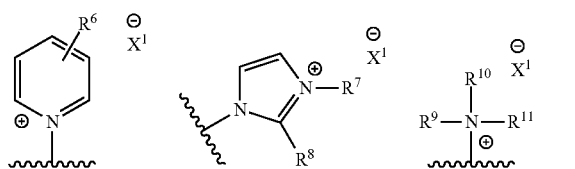

$R^2$ can also be hydrogen or a $C_1$ to $C_6$ alkyl;
$R^1$ can be a radical of formula (I bis) when the compound is formula I:

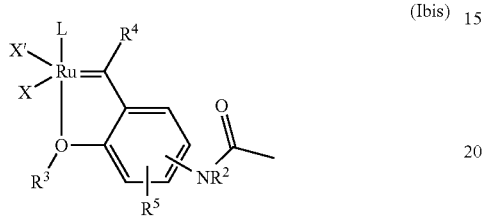

(Ibis)

$R^3$ is a $C_1$ to $C_6$ alkyl or a $C_5$ or $C_6$ cycloalkyl or a $C_5$ or $C_6$ aryl;
$R^4$, $R^5$, $R^6$, $R^7$, $R^8$, $R^9$, $R^{10}$, $R^{11}$ are, independently, hydrogen, a $C_1$ to $C_6$ alkyl, a $C_1$ to $C_6$ perhalogenoalkyl, or a $C_5$ or $C_6$ aryl; $R^9$, $R^{10}$, $R^{11}$ can form a heterocycle;
$X^1$ is an anion selected from the group consisting of halogen, tetrafluoroborate ($[BF_4]^-$), [tetrakis-(3,5-bis-(trifluoromethyl)-phenyl)borate] ($[BARF]^-$), hexafluorophosphate ($[PF_6]^-$), hexafluorantimonate ($[SbF_6]^-$), hexafluoroarsenate ($[AsF_6]^-$), and trifluoromethylsulfonate ($[(CF_3)_2N]^-$);
$R^1$ and $R^2$ can form with the N and the C to which they are attached a heterocycle of formula:

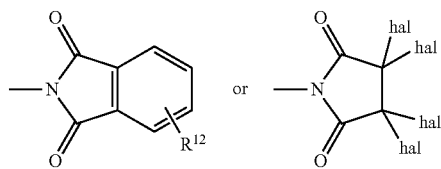

wherein hal is an halogen and $R^{12}$ is hydrogen, a $C_1$ to $C_6$ alkyl, or a $C_5$ or $C_6$ cycloalkyl or a $C_5$ or $C_6$ aryl.

2. Compound according to claim 1, wherein L is $P(R^{13})_3$, with $R^{13}$ being a $C_1$ to $C_6$ alkyl or an aryl or a $C_5$ or $C_6$ cycloalkyl.

3. Compound according to claim 1, wherein L is a ligand of formula 7a, 7b, 7c, 7d or 7e

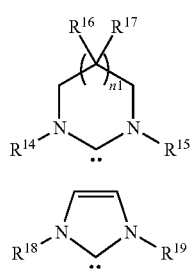

7a

7b

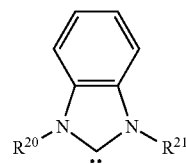

7c

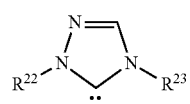

7d

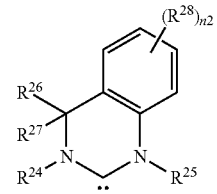

7e in which: $n^1$=0, 1, 2, 3;
$R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ are independently a $C_1$ to $C_6$ alkyl, a $C_3$ to $C_{20}$ cycloalkyl, a $C_2$ to $C_{20}$ alkenyl, a naphthyl, an anthracene or a phenyl, wherein said phenyl can be substituted by up to 5 groups chosen from the $C_1$ to $C_6$ alkyls, the $C_1$ to $C_6$ alkoxys and the halogens; $R^{16}$ and $R^{17}$, and $R^{26}$ and $R^{27}$ can form a cycle with 3, 4, 5, 6, or 7 links; $R^{28}$ can independently form an aromatic cycle with 6 conjoined links.

4. Compound according to claim 1, wherein L is $PCy_3$, with Cy being cyclohexyl, or L is a ligand of formula 7a or 7b, X is a chlorine, X' is a chlorine.

5. Compound according to claim 2, wherein the ion marker Y is selected from the group consisting of:

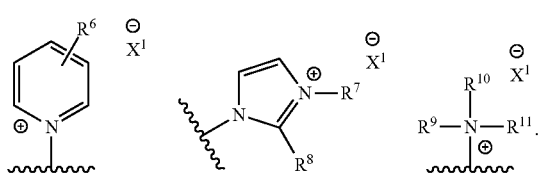

6. Compound according to claim 4, wherein $R^1$ is selected from the group consisting of $CF_3$, $C_6F_5$, and $pNO_2C_6H_4$.

7. Compound according to claim 6, wherein in(I) $R^1$ is $CF_3$.

8. Compound according to claim 4, wherein formula 1 is formula 1b:

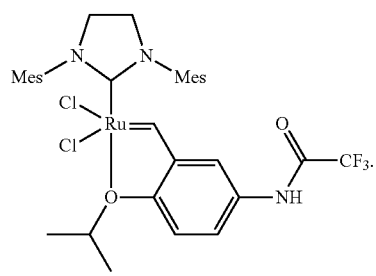

9. Compound according to claim 4, wherein formula 1 is formula 1c:

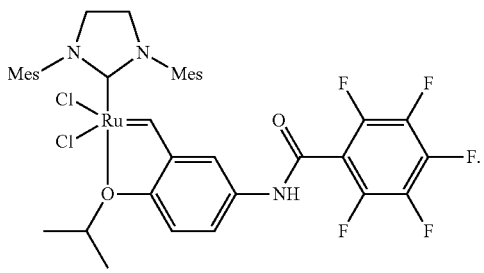

1g

10. Compound according to claim 4, wherein formula 1 is formula 1d:

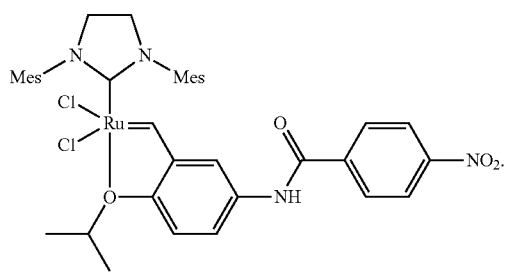

11. Compound according to claim 4, wherein formula 1 is formula 1e:

14. Compound according to claim 4, wherein formula 1 is formula 1h:

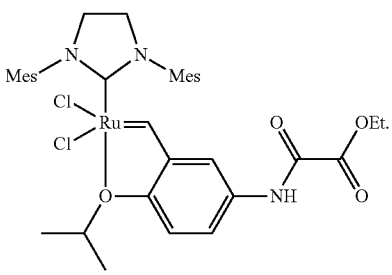

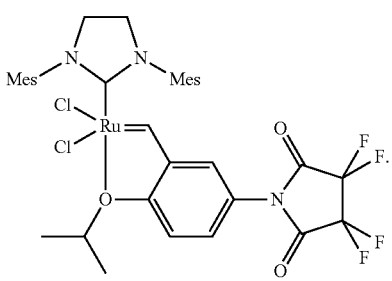

1h

12. Compound according to claim 4, wherein formula 1 is formula 1f:

15. Compound according to claim 4, wherein formula 1 is formula 1i:

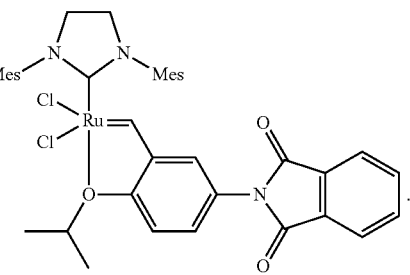

1i

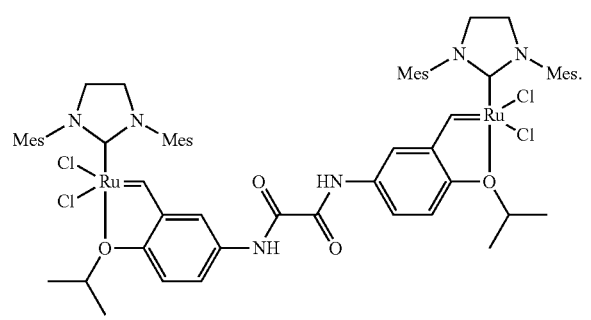

13. Compound according to claim 4, wherein formula 1 is formula 1g:

16. Compound according to claim 4, wherein formula 1 is formula 1j:

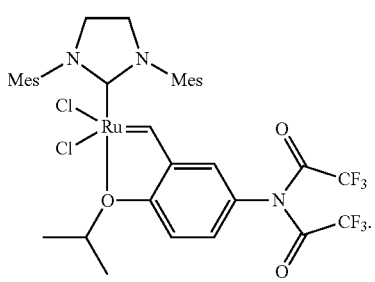

1j

17. Compound according to claim 4, wherein formula 1 is formula 1k:

18. Compound according to claim 4, wherein formula 1 is formula 11:

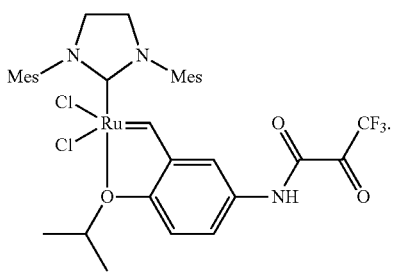

19. Compound according to claim 4, wherein formula 1 is formula 12:

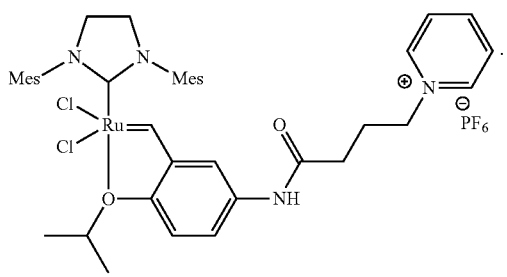

20. Compound according to claim 4, wherein formula 1 is formula 13:

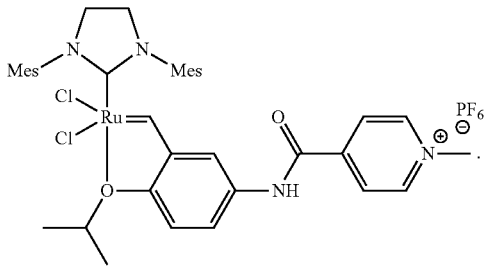

21. Compound according to claim 4, wherein formula 1 is formula 14:

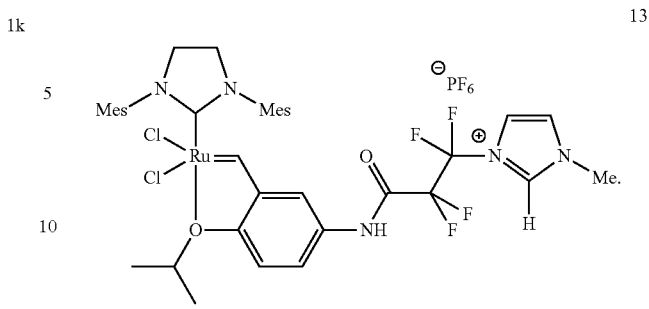

22. Method for synthesis of a compound according to claim 1, comprising a first step consisting of reacting 4-isopropoxy-3-vinylaniline with a compound having an acyl function so as to obtain an amide ligand and a second step consisting of reacting said amide ligand with a compound of formula (III):

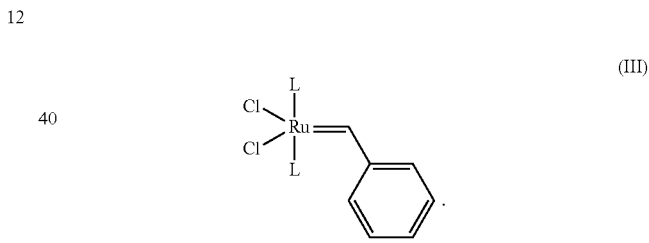

23. Method according to claim 22, wherein said compound of formula (III) is the Grubbs precatalyst (2b) or the Nolan precatalyst (2c).

\* \* \* \* \*